(12) United States Patent
Henderson

(10) Patent No.: US 10,336,416 B2
(45) Date of Patent: *Jul. 2, 2019

(54) SURFBOARD ACCESSORY FOR SURFBOARD RETENTION AND MEDICAL EMERGENCIES

(71) Applicant: Carson Thomas Henderson, Franklin, TN (US)

(72) Inventor: Carson Thomas Henderson, Franklin, TN (US)

( * ) Notice: Subject to any disclaimer, the term of this patent is extended or adjusted under 35 U.S.C. 154(b) by 265 days.

This patent is subject to a terminal disclaimer.

(21) Appl. No.: 15/259,021

(22) Filed: Sep. 7, 2016

(65) Prior Publication Data

US 2016/0375969 A1 Dec. 29, 2016

Related U.S. Application Data

(63) Continuation of application No. 14/726,579, filed on May 31, 2015, now Pat. No. 9,456,826, which is a (Continued)

(51) Int. Cl.
*A61B 17/00* (2006.01)
*B63C 9/00* (2006.01)
(Continued)

(52) U.S. Cl.
CPC .............. *B63C 9/00* (2013.01); *A61B 17/135* (2013.01); *A61B 17/1322* (2013.01);
(Continued)

(58) Field of Classification Search
CPC ............ A61B 17/1327; A61B 17/1322; A61B 17/1325; A61B 17/135; B63B 35/7933; B63B 2035/794; B63C 9/00
(Continued)

(56) References Cited

U.S. PATENT DOCUMENTS

| 35,038 | A | * | 4/1862 | Pierce | ............... A61B 17/1327 606/203 |
| 1,447,967 | A | * | 3/1923 | Rutledge | ............... A44B 11/25 24/163 R |

(Continued)

FOREIGN PATENT DOCUMENTS

| WO | 2015085124 A2 | 12/2014 |
| WO | 2015119968 A1 | 8/2015 |
| WO | 2016089446 | 6/2016 |

OTHER PUBLICATIONS

Written Opinion of the International Search Authority/US, dated May 22, 2015 on International Patent Application PCT/US14/68675, filed Dec. 5, 2014 in the name of Carson Thomas Henderson.
(Continued)

*Primary Examiner* — Amy R Weisberg
(74) *Attorney, Agent, or Firm* — Franklin & Associates International Inc.; Matthew F. Lambrinos

(57) ABSTRACT

A tourniquet device includes a tourniquet strap having an outward facing surface and an inward facing surface, the outward facing surface being covered with a plurality of hook fasteners, the inward facing surface having a section that is provided with a plurality of loop fasteners, a first end and a second end, the first end comprising a buckle, the second end having a cavity, and a securement strap configured for storage within the cavity, the securement strap including a terminal end that includes a pull tab, the securement strap is configured to be selectively placed in a stored position and a deployed position.

27 Claims, 25 Drawing Sheets

Related U.S. Application Data continuation-in-part of application No. PCT/US2014/068675, filed on Dec. 5, 2014.

(60) Provisional application No. 61/912,460, filed on Dec. 5, 2013.

(51) Int. Cl.
  *A61B 17/132* (2006.01)
  *B63B 35/79* (2006.01)
  *A61B 17/135* (2006.01)

(52) U.S. Cl.
  CPC ...... *A61B 17/1325* (2013.01); *A61B 17/1327* (2013.01); *B63B 35/7933* (2013.01); *B63B 2035/794* (2013.01)

(58) Field of Classification Search
  USPC .................................................. 606/201–204
  See application file for complete search history.

(56) References Cited

U.S. PATENT DOCUMENTS

| | | | | |
|---|---|---|---|---|
| 1,688,880 A * | 10/1928 | Pope | ...................... | A44B 13/00 2/50 |
| 1,870,052 A * | 8/1932 | Jones | ................ | A61B 17/1327 606/203 |
| 1,962,285 A | 6/1934 | Robinson | | |
| 2,017,948 A * | 10/1935 | Chenery | ............ | A61B 17/1327 606/203 |
| 2,113,534 A * | 4/1938 | Brown | ............... | A61B 17/1327 606/203 |
| 2,339,239 A * | 1/1944 | Carmichael | ............. | A41F 11/16 2/300 |
| 2,363,138 A | 11/1944 | Moore | | |
| 2,702,551 A * | 2/1955 | Hobson | .............. | A61B 17/1322 606/203 |
| 2,756,753 A * | 7/1956 | Means | ................ | A61B 17/1327 128/885 |
| 2,812,123 A * | 11/1957 | Girton | .................. | A47D 13/086 224/150 |
| 3,802,011 A * | 4/1974 | Castagnola | ......... | B63B 35/7933 24/3.13 |
| 3,931,656 A * | 1/1976 | Thomson | ............ | B63B 35/7933 441/75 |
| 4,041,562 A * | 8/1977 | Nealy | ................. | B63B 35/7933 24/3.2 |
| 4,044,415 A * | 8/1977 | Wood | .................. | B63B 35/7933 267/69 |
| 4,234,990 A * | 11/1980 | Colburn | .............. | B63B 35/7933 403/157 |
| 4,384,583 A * | 5/1983 | Speelman | .......... | A61B 17/1322 2/338 |
| 4,601,161 A * | 7/1986 | Drellich | ..................... | B68B 1/00 54/46.1 |
| 4,637,394 A * | 1/1987 | Racz | .................... | A61B 17/135 606/202 |
| 4,813,080 A * | 3/1989 | Toso | ................... | A41D 13/0007 2/44 |
| 4,938,040 A | 7/1990 | Humphreys, Jr. | | |
| 5,098,324 A * | 3/1992 | Isono | ................. | B63B 35/7933 428/100 |
| 5,194,026 A * | 3/1993 | Corwin | .............. | B63B 35/7933 280/637 |
| 5,295,996 A * | 3/1994 | Blair | .................. | A61B 17/1325 128/119.1 |
| 5,370,286 A * | 12/1994 | Newman | .................... | A45F 3/14 119/857 |
| 5,791,906 A * | 8/1998 | Robinson, Jr. | ......... | A63C 11/00 434/255 |
| 5,904,056 A | 5/1999 | Ozaki | | |
| 5,938,492 A * | 8/1999 | Carlini | ................ | B63B 35/7936 441/75 |
| 6,245,024 B1 * | 6/2001 | Montagnino | ...... | A61B 5/02233 600/499 |
| 6,471,560 B2 | 10/2002 | Kerckhoff | | |
| 6,899,720 B1 * | 5/2005 | McMillan | .......... | A61B 17/1322 606/203 |
| 6,960,223 B1 * | 11/2005 | Ambach | ............. | A61B 17/1327 606/203 |
| 7,604,651 B1 * | 10/2009 | Harris | ................. | A41D 13/1236 606/203 |
| 7,947,061 B1 * | 5/2011 | Reis | .................... | A61B 17/1322 606/203 |
| 8,348,970 B2 | 1/2013 | Janota | | |
| 8,465,514 B1 * | 6/2013 | Rose | ................... | A61B 17/1322 606/203 |
| 8,652,164 B1 * | 2/2014 | Aston | ................ | A61B 17/1327 606/203 |
| 9,168,044 B2 * | 10/2015 | Kirkham | ............ | A61B 17/1322 |
| 9,456,826 B2 * | 10/2016 | Henderson | ......... | A61B 17/1325 |
| 2003/0028215 A1 * | 2/2003 | Brooks | .............. | A61B 17/1327 606/203 |
| 2003/0139766 A1 * | 7/2003 | McEwen | .............. | A61B 17/135 606/203 |
| 2004/0173649 A1 | 9/2004 | Luedtke | | |
| 2005/0049630 A1 * | 3/2005 | Ambach | ............. | A61B 17/1327 606/203 |
| 2005/0113866 A1 * | 5/2005 | Heinz | ................ | A61B 17/1322 606/203 |
| 2005/0267518 A1 * | 12/2005 | Wright | ................. | A61B 17/132 606/203 |
| 2007/0005107 A1 | 1/2007 | Janota et al. | | |
| 2008/0243172 A1 * | 10/2008 | Thorpe | ............. | A61B 17/1322 606/203 |
| 2010/0049241 A1 * | 2/2010 | Persson | ............. | A61B 17/1322 606/203 |
| 2010/0057120 A1 | 3/2010 | Kirkham | | |
| 2010/0160957 A1 * | 6/2010 | Kirkham | ............ | A61B 17/1322 606/203 |
| 2011/0072545 A1 | 3/2011 | Bennett | | |
| 2011/0171861 A1 | 7/2011 | Roland | | |
| 2011/0270299 A1 * | 11/2011 | Rose | ................... | A61B 17/1322 606/203 |
| 2011/0271494 A1 * | 11/2011 | Bellamy | ................ | A44B 11/18 24/16 R |
| 2011/0295309 A1 | 12/2011 | Sullivan | | |
| 2011/0312233 A1 | 12/2011 | Starck, Jr. et al. | | |
| 2012/0158041 A1 * | 6/2012 | Craig | ...................... | A41D 1/06 606/203 |
| 2012/0215254 A1 | 8/2012 | Brub | | |
| 2012/0310273 A1 * | 12/2012 | Thorpe | ............. | A61B 17/1322 606/203 |
| 2013/0110019 A1 * | 5/2013 | Hopman | ............. | A61B 17/135 602/13 |
| 2013/0238014 A1 * | 9/2013 | Reynolds | .................. | F41H 1/02 606/203 |
| 2015/0257767 A1 | 9/2015 | Henderson | | |
| 2017/0360451 A1 * | 12/2017 | Strattner | ................ | B43K 29/00 |
| 2018/0257747 A1 * | 9/2018 | Haskins | ............. | B63B 35/7933 |

OTHER PUBLICATIONS

International Search Report of International Search Authority / US, dated May 22, 2015 on International Patent Application PCT/US14/68675, filed Dec. 5, 2014 in the name of Carson Thomas Henderson.

International Search Report of International Search Authority / US, dated Aug. 21, 2015 on International Patent Application PCT/US2015/033445, filed May 31, 2015 in the name of Carson Thomas Henderson.

Non-Final Office Action dated Feb. 24, 2016, Issued on U.S. Appl. No. 14/726,579, filed May 31 2015 in the name of Carson Thomas Henderson.

Non-Final Office Action dated Feb. 23, 2016, Issued on U.S. Appl. No. 14/869,992, filed Sep. 29 2015 in the name of Carson Thomas Henderson.

Swift-Strap LLC, Thor, webpage downloaded on Aug. 25, 2016 from the internet address http://www.thortq.com/, Swift-Strap llc, USA.

(56) References Cited

OTHER PUBLICATIONS

PCT/US16/50589 filed Sep. 7, 2016, entitled Amphibious Tourniquet Devices and Methods of Use.
U.S. Appl. No. 29/529,414, filed Jun. 5, 2015, entitled Water Sports Board Accessory by Carson Thomas Henderson , 23 pages.
U.S. Appl. No. 29/540,993, filed Sep. 30, 2015, entitled Amphibious Tourniquet by Carson Thomas Henderson, 22 pages.
The Written Opinion of International Search Authority / US, dated Aug. 21, 2015 on International Patent Application PCT/US2015/033445, filed May 31, 2015 in the name of Carson Thomas Henderson.
EPO European Search Report dated Sep. 7, 2017 issued on European Patent Application 14868532.4 from PCT/US2014/068675, filed Dec. 5, 2014, in the name of Henderson, Carson Thomsam, entitled "Surfboard Accessory for Surfboard Retention and Medical Emergencies".
EPO European Examination Report dated Jun. 20, 2018 issued on European Patent Application 14868532.4 from PCT/US2014/068675 filed Dec. 5, 2014, in the name of Henderson, Carson Thomsam entitled "Surfboard Accessory for Surfboard Retention and Medical Emergencies".
Australian Examination Report dated Oct. 17, 2016 issued on Australian Patent Application AU2014360372 from PCT/US2014/068675, filed Dec. 5, 2014, in the name of Henderson, Carson Thomsam, entitled "Surfboard Accessory for Surfboard Retention and Medical Emergencies".
Chinese Office Action dated Jan. 16, 2017 issued on Chinese Patent Application No. CN201490001310.9 from PCT/US2014/068675 filed Dec. 5, 2014, in the name of Henderson, Carson Thomsam, entitled "Surfboard Accessory for Surfboard Retention and Medical Emergencies".

\* cited by examiner

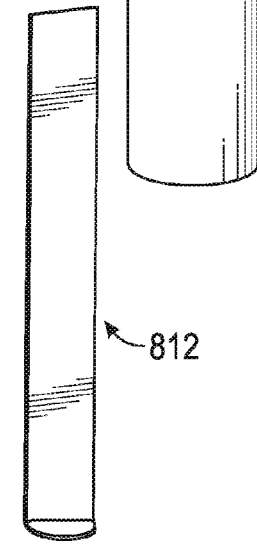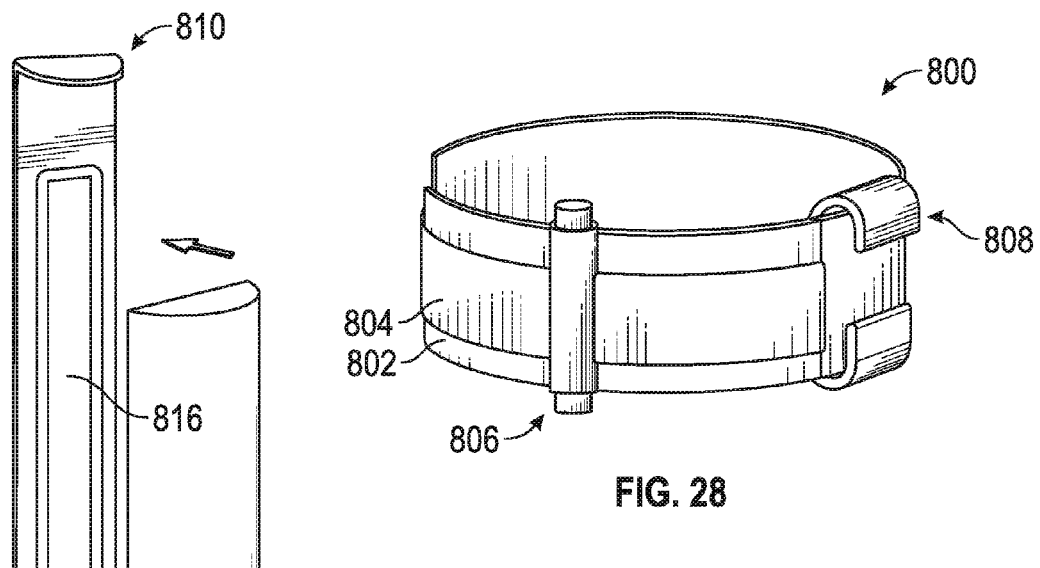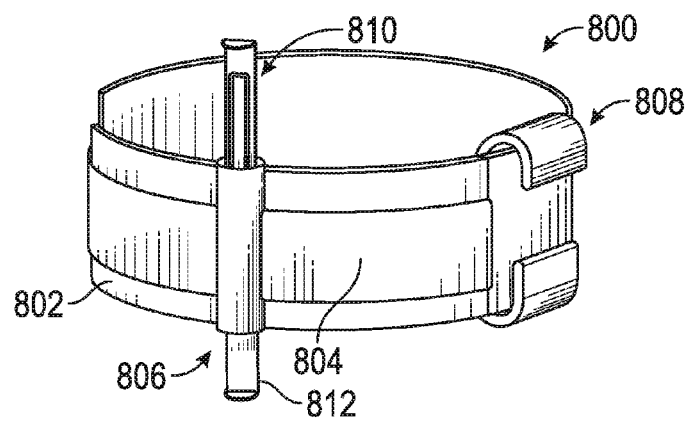
FIG. 29  FIG. 30

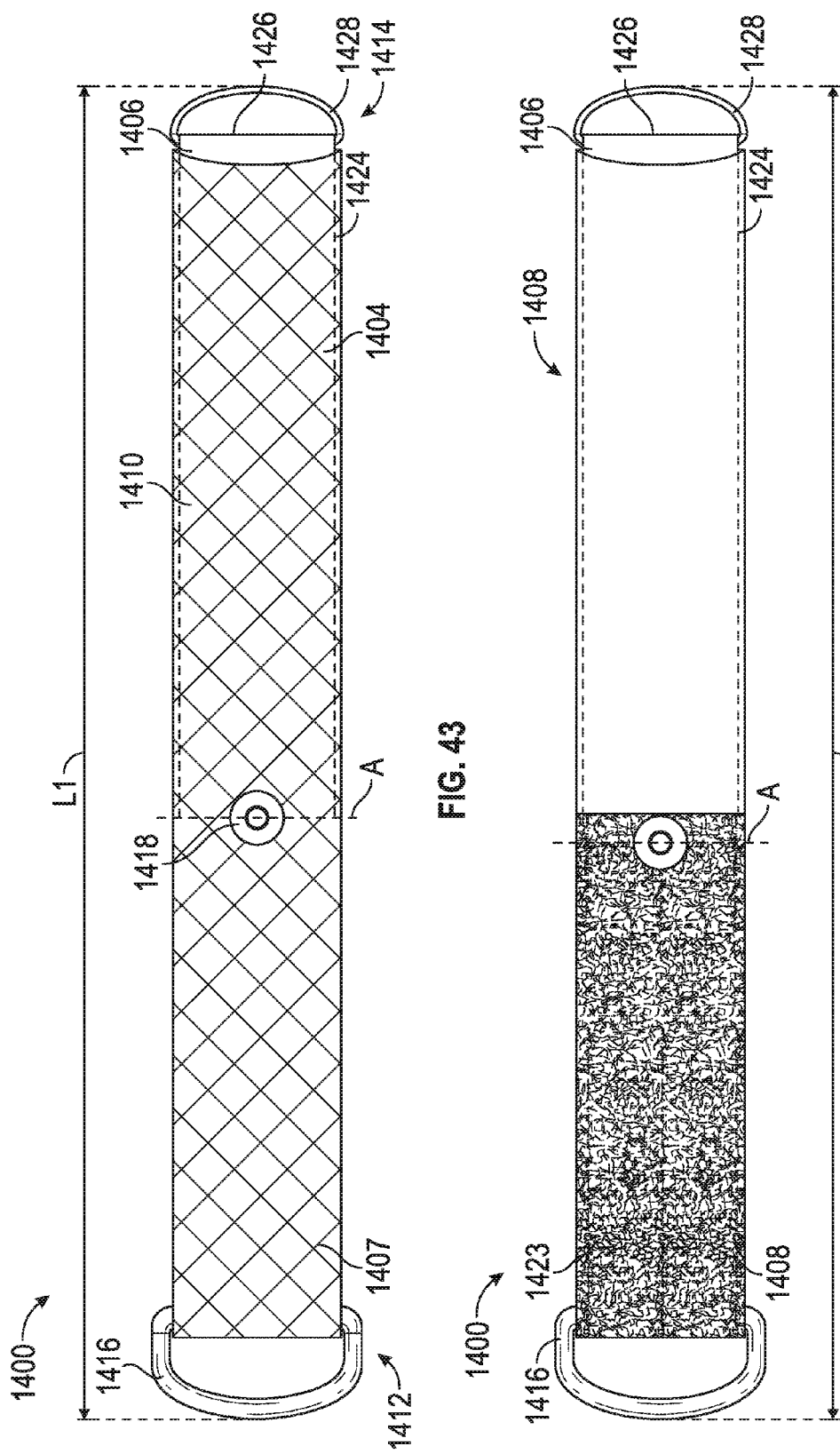

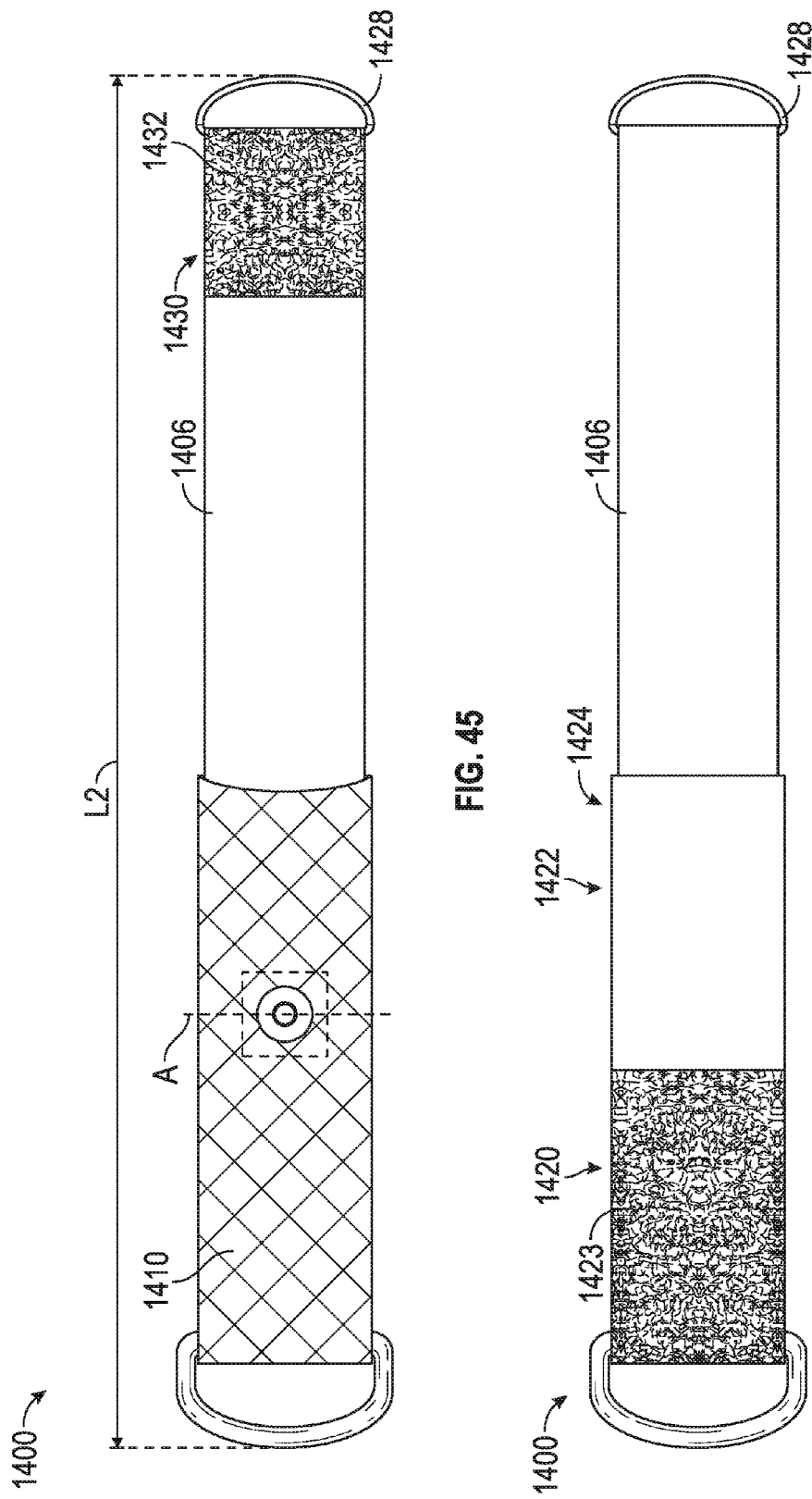

SURFBOARD ACCESSORY FOR SURFBOARD RETENTION AND MEDICAL EMERGENCIES

CROSS REFERENCE TO RELATED APPLICATIONS

This application is a continuation of U.S. Non-Provisional application Ser. No. 14/726,579, filed May 31, 2015, which is a continuation in part of International Patent Application PCT/US14/68675, filed Dec. 5, 2014, which claims the priority benefit of U.S. Provisional Application Ser. No. 61/912,460, filed on Dec. 5, 2013, all of which is hereby incorporated herein by reference including any reference cited therein.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERAL RIGHTS

N/A

TECHNICAL FIELD

Embodiments relate to surfboard accessories and, in particular but not exclusively, to surfboard accessories for surfboard retention. Embodiments also relate to methods of operating the surfboard accessories. Furthermore, embodiments relate to methods of manufacturing the surfboard accessories. Alternatively or additionally, embodiments relate to accessories for medical emergencies in one or more applications such as but not limited to military applications and water sports, and to methods of operating said accessories.

BACKGROUND

A surfboard leash is a surfboard accessory that is used for retention of a surfboard. The leash has a cord, typically made of urethane. One end of the cord is attachable to a surfer's ankle by a hook and loop cuff (Velcro™) and the other end is attachable to a fastener on the surfboard. Surfboard leashes enable a surfer to retain and prevent loss of the board at sea. This is advantageous when surfing big waves, where loss of the board could put the surfer in danger, and when surfing in crowded locations, where losing the board could be hazardous to other nearby surfers or swimmers.

There is a need to provide an improved surfboard accessory for use in surfboard retention Alternatively or additionally, there is a need to provide improved accessories for medical emergencies in military applications, watersports or other applications.

SUMMARY

According to one aspect, there is provided a surfboard accessory. The surfboard accessory can include a surfboard leash cuff band, wherein the cuff band comprises a body and a closure device carried on the body for closing the cuff band in a loop around an ankle of a surfer. A tourniquet assembly is integrated in the surfboard leash cuff band. A tourniquet strap storage component, can be carried on the cuff band and arranged to removeably store at least a portion of the tourniquet assembly such that, when the portion of the tourniquet assembly is so stored, the surfboard leash cuff band is closable around the ankle by the closure device and operable for surf retention without obstruction by the tourniquet assembly, and such that, when the tourniquet strap assembly portion is removed from the storage component, the surfboard accessory is arrangeable as a tourniquet for controlling extremity blood flow in the limb.

By blending both the surfboard leash cuff band and tourniquet into one seamlessly device, the surfboard accessory is not only capable of securing a surfboard to a surfer, but can also be used as a life-saving device thereby providing a technical and life-saving advantage as well as a psychological advantage.

According to another aspect, a surfboard accessory is provided that has a surfboard leash cuff band and a tourniquet assembly integrated in the cuff band. The cuff band comprises a body and a closure device carried on the body for closing the cuff band in a loop around an ankle of a surfer. The tourniquet assembly comprises a tourniquet strap and a strap-tensioning device. A portion of the tourniquet strap is extendable laterally beyond the length of the cuff band body to permit the strap to be secured in a loop around a limb and tightened by the strap-tensioning device to stop or control extremity blood flow in the limb. A tourniquet strap storage component is carried on the cuff band and arranged to removeably store in a folded configuration on the cuff band at least the tourniquet strap portion, wherein, when the tourniquet strap portion is so stored, the surfboard leash cuff band is closable around the ankle by the closure device and operable for surf retention without obstruction by the tourniquet assembly, and wherein, when the tourniquet strap portion is removed from the storage component, the surfboard accessory is operable as a tourniquet assembly for controlling extremity blood flow in the limb.

According to yet aspect, there is provided a kit of parts for assembling the surfboard accessory. The kit of parts can comprise a surfboard leash cuff band, wherein the cuff band comprises a body and a closure device carried on the body for closing the cuff band in a loop around an ankle of a surfer, a strap tensioning device, a tourniquet strap, wherein a portion of the tourniquet strap is extendable laterally beyond the length of the cuff band body to permit the strap to be secured in a loop around a limb and tightened by the strap tensioning device to stop or control extremity blood flow in the limb; and tourniquet strap storage component, carrierable on the cuff band and arranged to removeably store in a folded configuration on the cuff band at least a portion of the tourniquet strap such that the surfboard leash cuff band is closable around the ankle by the closure device without obstruction by the tourniquet strap. On assembly, when at least the tourniquet strap portion is so stored, the surfboard accessory is operable as a surfboard leash cuff band, and when the tourniquet strap portion is removed from the storage component, the surfboard accessory is operable as a tourniquet assembly for controlling extremity blood flow in the limb.

According to another aspect, a method of operating the aforesaid surfboard accessory is provided.

According to yet another aspect, a method of manufacturing the aforesaid surfboard accessory is provided.

In the aforementioned aspects, the tourniquet strap assembly may be in one example, a one-handed self-applying tourniquet assembly.

In some examples of the aforementioned aspects, the surf board leash cuff band, tourniquet strap, tourniquet cuff or any combination thereof is a webbing material, such as that typically used in seat belt webbing. The webbing may be a polyester webbing or a webbing made from, or including, a synthetic polymer such as but not limited to nylon.

According to some embodiments, the present technology is directed to a tourniquet device, comprising: (a) a first strip of material having a length and a longitudinal axis; (b) a second strip of material having a first end and a second end, the first end and the second end being attached to the first strip of material, the second strip of material overlaying the first strip of material and extending along the longitudinal axis of the first strip of material, the first strip of material and the second strip of material forming a loop that is configured to encircle an appendage of an individual; and (c) a windlass device coupled with the second strip of material in such a way that turning the windlass device reduces a diameter of the loop to apply pressure to the appendage.

According to other embodiments, the present technology is directed to a tourniquet device, comprising: (a) a belt having a continuous strip of material disposed in an inside pocket of the belt, the belt comprising an external pocket that receives at least a portion of a length of the belt therein; (b) a windlass device coupled to the continuous strip of material through an opening in the belt; and (c) a windlass securement member disposed proximate the windlass device, wherein the windlass device is wound to reduce a diameter of the continuous strip of material, and portion of the windlass device is locked in the windlass securement member, preventing the windlass device from unwinding.

According to some embodiments, the present technology is directed to a tourniquet device, comprising: (a) a belt section configured to encircle an appendage of a user, wherein a portion of the belt section is disposable within a pocket formed into the belt section, the portion is associated with a pull tab; (b) an inflatable tube in association with the belt section; (c) a port coupled with the inflatable tube; and (d) an interface for receiving a leash.

According to some embodiments, the present technology is directed to a tourniquet device comprising: (a) a belt having a continuous strip of material disposed in an inside pocket of the belt, the belt comprising an external pocket that receives at least a portion of a length of the belt therein; and (b) a ratchet windlass device coupled to the continuous strip of material through an opening in the belt, wherein the ratchet windlass device is used to reduce a diameter of the belt.

In yet other aspects of the present technology, a kit of parts for assembling any one or more of the aforementioned embodiments is provided. The kit of parts comprises the parts of the particular device and optionally a box or bag, and an instruction manual for assembling said device from said kit of parts; wherein said device parts and said instruction manual are carried in said box or bag.

According to some aspects, the aforementioned embodiments are configured for battlefield or military scenarios where individuals may have need for tourniquet. The devices of the present technology can be worn around an appendage or stored on the individual until the tourniquet needs to be deployed and used. Thus, in some aspects of the present technology, the devices need not include an interface for a leash or tether, although some embodiments provided herein include such interfaces.

In yet other aspects of the present technology, a tourniquet device comprises: (a) a tourniquet strap comprises: (1) an outward facing surface and an inward facing surface, the outward facing surface being covered with a plurality of hook fasteners, the inward facing surface comprising a section that is provided with a plurality of loop fasteners; (2) a first end and a second end, the first end comprising a buckle, the second end comprising a cavity; and (b) a securement strap configured for storage within the cavity, the securement strap comprising a terminal end that includes a pull tab, the securement strap is configured to be selectively placed in a stored position and a deployed position.

In yet other aspects of the present technology, a tourniquet device comprises: (a) an outward facing surface and an inward facing surface, the outward facing surface being covered with a plurality of hook fasteners, the inward facing surface comprising a section that is provided with a plurality of loop fasteners; (b) a first end and a second end, the first end comprising a buckle; (c) a securement strap configured for storage within the second end, the securement strap is configured to be selectively placed in a stored position and a deployed position; and (d) wherein the tourniquet strap is configured to apply pressure to an appendage of an individual by: (i) extending the securement strap from the stored position to the deployed position; (ii) looping the securement strap through the buckle; and (iii) wrapping the securement strap around the appendage to prevent loss of blood from the appendage.

In yet other embodiments, one or more of the features of one of the aforementioned aspects or embodiments of a tourniquet device is combined with features of one of the other aforementioned aspects or embodiments.

In yet other aspects, a kit of parts is provided for assembling any one or more of the aforementioned aspects or embodiments of the tourniquet device. In some embodiments, the kit of parts comprises the aforementioned elements of the one or more aforementioned aspects/embodiments of the tourniquet device and optionally a box or bag, and an instruction manual for assembling the device from the kit of parts; wherein said device parts and said instruction manual are carried in said box or bag.

DESCRIPTION OF THE DRAWINGS

FIG. 28 is a perspective view of a tourniquet device with a windless device that pin locks that use a slide rail, constructed in accordance with another embodiment of the present technology.

FIG. 29 illustrates the pin locks in an extended or unlocked position.

FIG. 30 illustrates the windless device in an extended or unlock configuration on the tourniquet device.

FIG. 43 is a front elevational view of another tourniquet device of the present technology.

FIG. 44 is a rear elevational view of the tourniquet device of FIG. 43.

FIG. 45 is a front elevational view of the tourniquet device of FIGS. 43 and 44 in an extended position.

FIG. 46 is a rear elevational view of the tourniquet device of FIGS. 44-45 in an extended position.

DETAILED DESCRIPTION OF THE PREFERRED EMBODIMENTS

Figure 1:
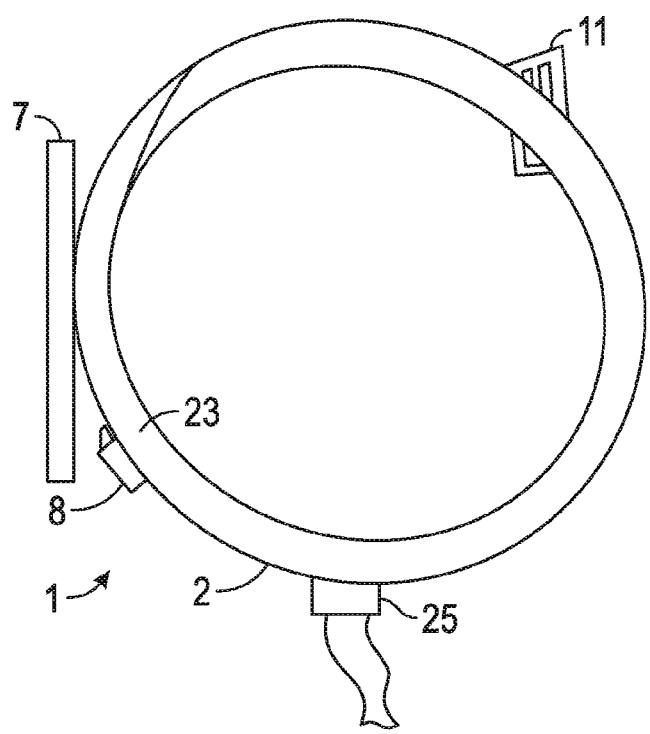
FIG. 1 depicts a side elevation view of a surfboard accessory in a surfboard retention operating configuration in which the cuff band is closed in a loop according to one embodiment.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Technical features described in this application can be used to construct various embodiments of a surfboard accessory. In one approach, the surfboard accessory is a surf tourniquet comprising a hybrid combination of a surfboard leash part and a tourniquet, such as a one-handed self-applying tourniquet. A closed loop windlass operated tourniquet system may be utilized. The tourniquet is embedded into the part of a surfboard leash that attaches to the ankle. When needed, the leash can be detached from the ankle cuff and the embedded tourniquet portion can be adjusted to fit the arm or leg and subsequently tightened to stop or control extremity blood flow. Furthermore, a windlass bar for twisting the strap, or other strap-tensioning device, can be operated to provide more or less pressure with ease.

The surfboard leash part exists to help a surfer maintain control of their surfboard, while the tourniquet, when properly applied, can save a limb by stopping massive bleeding wounds. Furthermore, in one example, the windlass operation of the tourniquet enables the user to apply circumferential pressure one-handed to stop bleeding.

The surfboard accessory of the embodiments, referred to herein as the Surf Tourniquet, blends both part of the surfboard leash and tourniquet into one seamlessly device that not only secures a surfboard to a surfer, but can also be used as a life-saving device thereby providing not only a technical and life-saving advantage, but a psychological advantage as well.

Reference will now be made to the drawings in which the various elements of embodiments will be given numerical designations and in which embodiments will be discussed so as to enable one skilled in the art to make and use the invention.

Specific reference to components, process steps, and other elements are not intended to be limiting. Further, it is understood that like parts bear the same reference numerals, when referring to alternate figures. It will be further noted that the figures are schematic and provided for guidance to the skilled reader and are not necessarily drawn to scale. Rather, the various drawing scales, aspect ratios, and numbers of components shown in the figures may be purposely distorted to make certain features or relationships easier to understand. The term "carried" is used herein to mean mounted on or to, integrated with, fixed on or to, or otherwise combined with.

Figure 2:
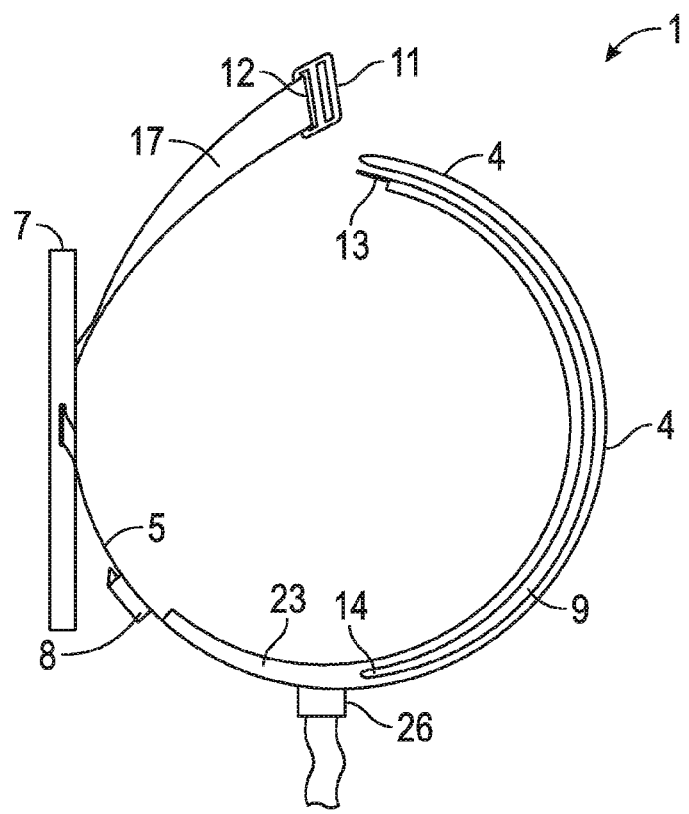
FIG. 2 is a side elevation view of the surfboard accessory with the cuff band about to be closed together to form the loop shown in FIG. 1.
Figure 3:
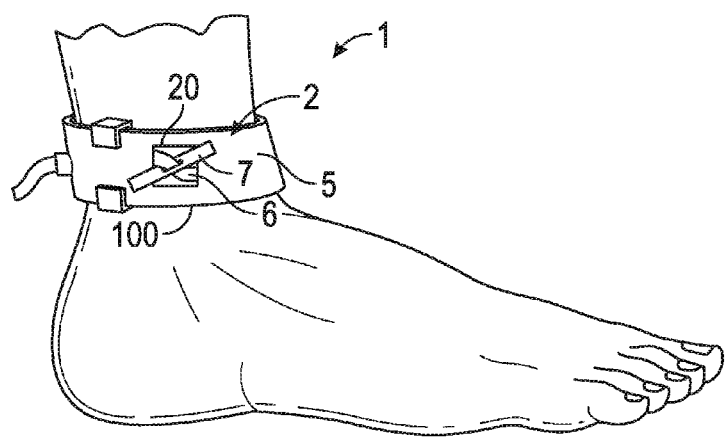
FIG. 3 is a side view of the surfboard accessory configured as shown in FIG. 1 and in which the cuff band is closed around the ankle of a surfer for use in surfboard retention.

Referring to one embodiment shown in the accompanying drawings, FIGS. 1 & 2 depict side views of the surf tourniquet in surfboard retention operating configurations in which the cuff band is closed and almost closed, respectively, and FIG. 3, depicts an outer side view of the surf tourniquet in a surfboard retention operating configuration in which the cuff band body has been strapped and closed around the ankle 100 of a human surfer. As a general outline, surf tourniquet 1 has a surfboard leash cuff band 2 and a tourniquet assembly 6-11 integrated in the cuff band.

As shown in FIGS. 1-3, surfboard leash cuff band 2 has a body 5 having a first end 12, and a second end 13 opposite the first end 12. In the example shown in the figures, cuff band body 5 is generally elongated and planar in configuration and has a hollow longitudinal interior. In other examples, other shaped configurations may be adopted. Cuff band body 5 is for example made from a sheet or strip of material, such as but not limited to a synthetic polymer nylon, grow ribbon, elastic, polyester, hook and loop fastener material or any combination thereof. Non-limiting examples of such hook and loop fastener material are, Velcro (Velcro is a Trade Mark of Velcro Industries B.V. LIMITED LIABILITY COMPANY NETHERLANDS Castorweg 22-24 Curacao NETHERLANDS), or self-engaging fastener material which is material with hook and loop woven on the same surface, such as snag-free fasteners known as Omni-tape (Omni-tape is a Trade Mark of Velcro Industries B.V. LIMITED LIABILITY COMPANY NETHERLANDS Castorweg 22-24 Curacao NETHERLANDS). In another example, the body material may be, or include, a thermoplastic polymer. For example, the thermoplastic body material may be or include polypropylene.

Body 5 may be formed as a single piece or section of such material or as any combination of sections or straps of the material, as needed.

In one embodiment, body 5 is made from webbing material, such as that typically used in seat belt webbing. The webbing may be a polyester webbing or a webbing made from, or including, a synthetic polymer such as but not limited to nylon.

Figure 4:
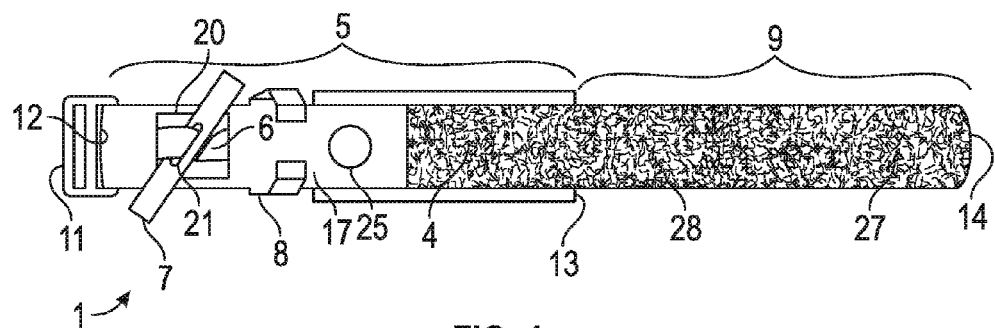
FIG. 4 is an outer side, plan view of the surfboard accessory of FIG. 1 in a tourniquet operating configuration with a tourniquet cuff and strap fully extended according to one embodiment.
Figure 5:
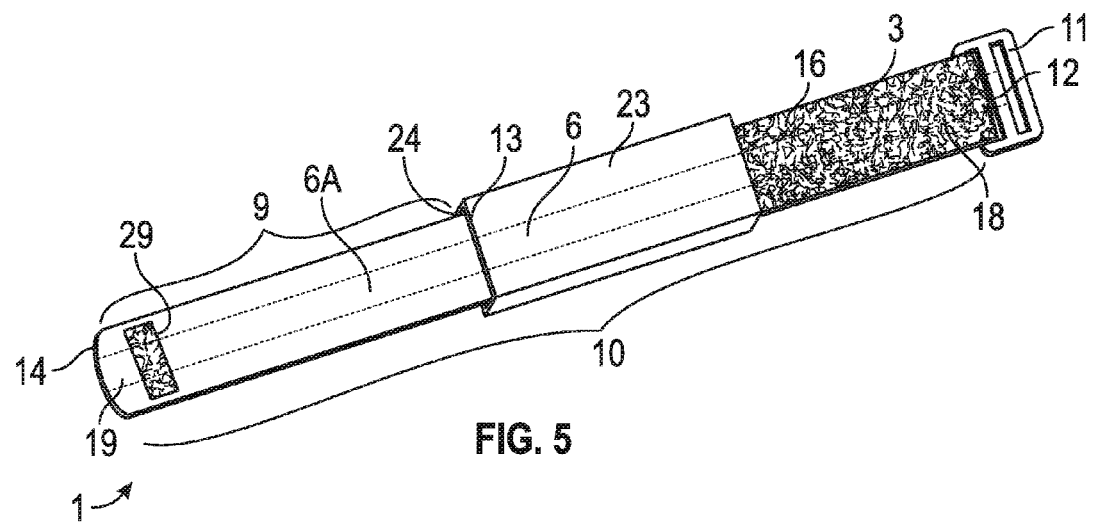
FIG. 5 is an inner side, plan view of the surfboard accessory configured as shown in FIG. 4.

As best shown in FIGS. 4 & 5, which respectively depict outer and inner side plan views of the surf tourniquet of FIG. 1 in a tourniquet operating configuration according to one embodiment, cuff body 5 has, on the outer side, a substantially planer and longitudinal outer wall 17 and, on the inner side, a substantially planar and longitudinal inner wall 16. When cuff band 2 is placed around ankle 100 (see FIG. 3), inner wall 16 faces towards the ankle and outer wall 17 faces away from the ankle.

A closure device is carried on cuff band body 5 such that, when cuff band body 5 is strapped around ankle 100, cuff band 2 is closable in a loop around the ankle by the closure device. For example, the closure device is a fastener configured to releasably interconnect cuff band body first and second ends 12,13 together (see FIG. 3).

In the example of cuff band 2 shown in FIGS. 1-3, the closure device comprises a pair of mating members configured to releasably attach to one another. In the example, the mating members are strips of a hook and loop fastener, such as but not limited to a Velcro™ hook and loop fastener. The hook and loop fastener may be made from a polyester, polypropylene, aramid, stainless steel, or any combination thereof to suit desired performance and aesthetic characteristics. One hook strip 3 is attached on body inner wall 16 at or proximate body first end 12 and the mating loop strip 4 is attached along body outer wall 17 and extending from body second end 13 towards first end 12. Alternatively, the hook strip is arranged on second end 13 and the loop strip on first end 12. In other examples, the closure device is made from a self-engaging fastener such as snag-free fasteners known as Omni-Tape™ in which the hook and loop is woven on the same surface of both first and second ends 12,13. In other embodiments the hook and/or loop strips can be in the form of snapping buttons. Other examples of the closure device are Velcro and snapping buttons on the end with male and female buttons on different sides, hook and loop arrangements flip-flopped. The closure device may be any type of fastener known or future developed fastener capable of releasably closing the cuff band in a loop around the ankle.

A surfboard lease cord attachment 25, is fixedly attached to surfboard leash cuff body 5, for releasably attaching a surfboard leash cord 26 to cuff body 5. Surfboard leash cord 26 may be a urethane cord or other surfboard leash cord material. Attachment 25 is disposed on the cuff body outer wall 17 and generally centrally between first and second ends 12,13 thereof. In other examples, leash attachment 25 may be placed in other positions on the body and/or leash cord 26 is permanently attached to the cuff band 2.

Referring now in more detail to the tourniquet assembly, the assembly has a tourniquet strap 6 for looping around a limb, such as a thigh 200 (see FIG. 6) and a tourniquet strap tensioning device for adjusting the tourniquet strap loop circumference and thereby the tension of the strap loop around the limb. In the example of surf tourniquet 1 shown in the accompany figures, the tourniquet assembly is a one-handed self-applying tourniquet which has a longitudinal tourniquet cuff 10 for longitudinally carrying and covering tourniquet strap 6.

Longitudinal tourniquet cuff 10 is defined by surfboard leash cuff body 5 and a lateral cuff extension portion 9 extending laterally from cuff body second end 12. Lateral cuff extension portion 9 is either integrated seamlessly with cuff band 2 or is a separate piece of material. Lateral cuff extension portion 9 is formed from a sheet or sheets of material, such as but not limited to nylon, grow ribbon, elastic, synthetic polymer, polyester, hook and loop fastener material, or any combination thereof. Non-limiting examples of such hook and loop fastener material are, Velcro™, or self-engaging fasteners with hook and loop woven on the same surface such as snag-free fasteners known as Omni-Tape™. In another example, the material may be or includes a thermoplastic polymer. For example, the thermoplastic body material may be or include polypropylene.

Velcro™, or any combination thereof. Lateral cuff extension 9 is formed as a seamless lateral extension of the cuff body material or may be a separate piece of material that that has one end fixedly attached, for example but not limited to by stitching, to cuff body second end 13. Lateral cuff extension 9 and body 5 may be formed together as a single long strip of material or made up of any combination of strips or sections of the material, as needed. In one embodiment, lateral cuff extension 9 is made from webbing material, such as that typically used in seat belt webbing. The webbing may be a polyester webbing or a webbing made from, or including, a synthetic polymer such as but not limited to nylon.

In the figures, lateral cuff extension portion 9 is slightly narrower than the width of surfboard leash cuff body 5 but, in other examples, cuff extension 9 may be of the same width or even wider than cuff body 5.

Both surfboard leash cuff body 5 and lateral cuff extension portion 9 have longitudinal hollow interiors in line end-to-end with one another so as to define a single longitudinal interior spanning tourniquet cuff 10 in which tourniquet strap 6 is longitudinally disposed.

Tourniquet strap 6 is made of nylon or other suitable tourniquet trap material. Tourniquet strap 6 is a longitudinal strap member having a first end 18, and second end 19, opposite first end 18. Strap first end 18 is fixed to surfboard leash cuff band 2 at, or proximate, cuff body first end 12. Second end 19 of tourniquet strap 6 is fixed to cuff extension 9 at or proximate the distal end 14 thereof. Since strap 6 is narrower than the tourniquet cuff hollow interior, the strap portion between strap fixed ends 18,19 is free to move relative to the tourniquet cuff 10.

As best shown in FIG. 5, tourniquet strap 6 extends along a length of cuff body 5 between cuff body first end 12 and extension distal end 14 and includes a portion 6A extending laterally from second end 13 beyond surfboard leash cuff band 2. Tourniquet strap 6, including portion 6A, is of a length sufficient to permit tourniquet strap 6 to be looped around the thigh or other limb 200 when the cuff body is placed on the limb. Whilst strap 6 and tourniquet cuff 10 are generally planar in the figures, strap 6, surfboard leash cuff body 5, and/or lateral cuff extension portion 9 may alternatively be of a circular or other cross section. Sizes of tourniquet strap 6, surfboard leash cuff body 5, and lateral cuff extension portion 9 vary according to application requirements and are typically 1 two 2 inches in width.

As best shown in FIG. 4, body outer wall 17 has an opening 20 to the longitudinal interior of body 5 and exposing a twistable portion of tourniquet strap 6 disposed in the body. The exposed strap portion cooperates with the tourniquet strap tensioning device. In the example of the figures, the strap tensioning device is a windlass bar 7 or other windless mechanism pre-threaded via an aperture 21 thereof onto the exposed twistable portion of the strap. As a substantial length of tourniquet strap 6 between fixed strap first and second ends 18, 19 is freely mounted in the longitudinal interior of tourniquet cuff 10, the strap portion between the strap fixed ends is twistable generally on itself by manually rotating windless bar 7 about a rotational axis generally perpendicular to the longitudinal axis of strap 6. In this manner, when tourniquet strap 6 is securely looped around a limb 200, twisting of the strap on itself by rotating windless bar 7 causes tourniquet strap 6 to pinch and reduce the circumference of the loop. A bar holder 8 is fixed to cuff body 5 for locking the bar 7 in position after rotation and thereby holding the twisted strap 6 under tension. The bar holder is typically configured to thread onto the entire cuff body, but in other examples may be configured to thread onto only one portion or section of the cuff. Opening 20 may be formed by suitable means and may be of any shape and size to allow windlass bar 7 to be manually operable to twist strap 6.

In other examples, the windlass bar or other windless mechanism is configured to be detachable from the surf tourniquet. Alternatively or additionally the windlass mechanism is a retractable windlass bar or other mechanism. In one example, the retractable windlass mechanism is a telescopic windlass bar having a series of interlocking segments or portions configured to be extendable and retractable as necessary to enable the bar to be configurable between an operating configuration and a retracted configuration. In the operating configuration, the telescopic segments or portions of the windlass bar are extended out to a sufficient length and interlock to enable the windlass bar to be manually operated to twist the strap. In the retracted configuration, the telescopic segments or portions are nested together such that the bar length is reduced and the bar can be conveniently stored on the cuff body or elsewhere when not in use.

The tourniquet assembly integrated in the surfboard leash cuff band also includes a tourniquet strap adjuster permanently fixed to cuff body 5 to permit lateral cuff extension portion 9, and tourniquet strap portion 6A disposed therein, to be engaged with the adjuster to thereby close, and coarsely tighten, tourniquet cuff 10 and strap 6 in a loop around limb 200 preparatory to tightening of tourniquet strap 6 by the windless bar 7. In the example of the surf tourniquet 1 shown in the figures, the tourniquet strap adjuster, which in this particular example is a triglide or other buckle 7, is fixedly attached to the cuff body first end 12.

Both tourniquet strap 6 and lateral cuff extension portion 9 are of a sufficient length so that, when the apparatus is placed on limb 200, tourniquet cuff 10, and strap 6 therein, can be closed in a loop around limb 200 using buckle 7. In the example surf tourniquet 1 of the figures, buckle 7 is attached length ways along the traverse edge of cuff body first end 12 and is sized to cooperate with cuff extension distal end 14 to thereby close the tourniquet cuff and strap in a loop.

In one example, a hook and loop fastener 27, or other fastener, is arranged on the outer wall of lateral cuff extension 9 at, or proximate, distal end 14 thereof (see FIG. 4) for mating with a cooperating hook and loop fastener 28 on the outer wall of tourniquet cuff 10. The fasteners 27, 28 spaced apart such that a portion of cuff extension 9 that has been fed through buckle 7 can be secured back over ton on cuff 10 using the fasteners. In one example, hook and loop fastener 4, in addition to hook and loop fastener 27, 28, may be collectively provided by a single strip of hook and loop fastener material extending along the outer wall of both the lateral cuff extension and a portion of the cuff body as shown in FIG. 4.

A storage component is carried on surfboard leash cuff band 2 and adapted and arranged to receive and removeably store, in a folded configuration, lateral cuff extension portion 9 including tourniquet strap portion 6A. One example of the storage component is a pocket or sleeve 23, or other open ended storage receptacle 23. Sleeve 23 is substantially planar and extends longitudinally along cuff body inner wall 16 between the cuff body first and second ends 12, 13.

Sleeve 23 is formed for example from two sheets of material sewed together along their longitudinal edges and then sleeve 23 sewn to cuff body inner wall 16. Sleeve sheet material may be a synthetic rubber, such as neoprene, for cushioning but may another material such as but not limited to nylon, polyester, etc. or any combination of such materials.

Sleeve 23 has an opening 24 that it is adapted and arranged for receiving, a portion of tourniquet cuff 10 and strap therein. In the example surf tourniquet 1 shown in the figures, sleeve opening 24 is substantially aligned with cuff body second end 13 and traverses the body such that lateral cuff extension 9 can be folded over onto the extension inner wall to enable cuff extension distal end 14 to be fed through sleeve opening 24 and the extension portion 9 to be tucked away in sleeve 23. FIG. 2 shows cuff extension 9 housed in sleeve 23 in the folded configuration. Cuff extension portion 9 has effectively been flipped over from the extended position shown in FIG. 5. in which the extension inner wall faced inwardly, into the stored position shown in FIG. 2, in which the inner wall now faces outwardly. Sleeve 23 is dimensioned to allow the entire length, or a substantial length of cuff extension portion 9 to be stored away in the sleeve. By adapting and arranging sleeve 23 on surfboard leash cuff band 2 in this manner, a portion of tourniquet strap 6 and tourniquet cuff 10 exceeding the length of cuff band 2 can be folded and stored out of the way in sleeve 23 so as to allow normal use of the surfboard leash cuff band without obstruction by the tourniquet assembly and without being significantly visible when the surfboard leash cuff band is placed around the ankle.

Furthermore, sleeve 23, filled with cuff extension portion 9 serves as a cushion or padding. In one example, storage sleeve 23 extends along a sufficient length of cuff body 5 such that sleeve 23 forms a complete cushion extending 360 degrees around the ankle when the cuff band is closed around the ankle by the closure device 3,4 as indicated in FIGS. 1 and 3. In order further to enhance cushioning, in one embodiment, sleeve 23 comprises a neoprene sleeve or is made from other synthetic rubber, or other materials. In one example, sleeve 23 is made from a nylon, polyester or other strap material and has a cushion backing on the interior or inner wall of the sleeve. For example, sleeve 23 is made from a webbing material, such as nylon or polyester webbing, as used in seat belt webbing, and has a piece of neoprene backing on the inner wall of sleeve 23 for cushioning against the users skin.

In other examples, the storage sleeve is of a reduced length but still forms a substantial cushion around the ankle or may only form a less than substantial cushion around the ankle. In other examples, sleeve 23 is carried on outer wall 17 of cuff body 5.

In one example, a hook and loop fastener, or other type of fastener, 29 is placed on the inner wall of lateral cuff extension portion 9 and an inside wall of sleeve 23 for securing the inner wall of the stored cuff extension portion to the inside wall of the sleeve. Cuff extension 9 may be secured to the cuff band in other ways.

In other embodiments, a storage compartment, other than a sleeve or other open ended receptacle, is envisaged. For example, a zipper or flap of material is adopted for the storage of the tourniquet strap. In one example, the tourniquet strap portion may be stowed within a zippered compartment that allows for normal and emergency use. In another example, the tourniquet strap portion may alternatively or additionally be stowed within a flap of overlapped material that allows for normal and emergency use.

As can be seen by way of exemplary embodiments, by integrating the tourniquet assembly and storage sleeve or other storage compartment into the surfboard cuff band in the aforementioned manner, the surf tourniquet is configurable between a surfboard retention operating configuration, in which the lateral cuff extension and strap are stored away in the sleeve or other storage compartment and the surf tourniquet functions as a surfboard leash cuff band for normal use in surfing, and a tourniquet operating configuration, in which the tourniquet cuff extension and strap are removed from the sleeve or other storage compartment and the surf tourniquet functions as a closed loop tourniquet medical device.

The surf tourniquet solves the problem of having an accessible means to first aid in the event of a shark attack, or other potentially fatal injuries that may be incurred by surfers, boogie boarders, or swimmers. It has been proven in combat that tourniquets can be worn for multiple hours before necrosis develops. This application provides a medium for everyone from the novice surfer, to travelling surfers to perform self-aid, or buddy-aid, and gives first responders and paramedics a greater chance to treat and save patients if properly and timely applied.

In one example, a kit of parts for assembling Surf Tourniquet 1 is provided. Surfboard leash cuff band 2, strap tensioning device 11, tourniquet strap 6, and storage component 23 are provided in a box or bag together with an instruction manual for assembling the kit of parts together to provide the surfboard accessory.

Other embodiments of the surf tourniquet that have similar, or at least some, benefits of surf tourniquet 1 are envisaged. For example, in the surf tourniquet of the accompany figures, the tourniquet strap is essentially an internal strap that is substantially hidden from view inside the tourniquet cuff. However, in other embodiments, the tourniquet strap may be more visible. In one embodiment, the tourniquet strap may be carried on the outer or inner wall of the tourniquet cuff by loops longitudinally distributed along the length of the cuff instead of being an interior strap housed within the tourniquet cuff.

In yet other embodiments of the surf tourniquet, some strap holes run internally under the surfboard leash connector.

The lateral cuff extension member may be stored on or in the storage component in other ways. For example, in one embodiment, the storage component may be one or more clips or fasteners mounted on the cuff body rather than a sleeve or pocket.

In yet another embodiment, the strap tensioning device may be a ratchet tensioning mechanism rather than a windless bar. The ratchet mechanism is arranged to engage with the tourniquet strap and is operable to shorten or lengthen the tourniquet strap circumference to tighten or loosen the strap loop and thereby increase or decrease the circumferential pressure around the limb. In another example, a clasp, or a circular winding ratchet system may be employed that differentiates from the aforementioned traditional ratchet system.

In yet another embodiment, part of or the entire lateral cuff extension portion may be omitted while the cuff body still serves to carry the tourniquet strap. In such embodiments, the tourniquet strap and strap adjuster are adapted to directly engage one another to close the strap in a loop without the cuff extending around the entire circumference of the limb.

In yet other embodiments, the strap adjuster is omitted and the tourniquet strap is carried on the cuff body with or without a lateral cuff extension portion member. The tourniquet strap has opposite distal ends, which are free running and extendable from corresponding opposite ends of the cuff body (i.e. the tourniquet strap ends 17, 18 are not fixed to the cuff material. Closing of the tourniquet strap loop preparatory to tightening by the windless by may be achieved by securing the strap free ends together.

A method of operating a surf tourniquet according to one embodiment will now be described with reference to the accompanying drawings.

Surfboard Retention Operating Configuration—Non-Emergency

During surfboard retention use or non-emergency use of surf tourniquet 1, surf tourniquet 1 is in the surfboard retention configuration in which tourniquet cuff 10 including strap portion 6A are stored away within sleeve 23 as described hereinbefore and shown in FIGS. 1-3. Let us assume that a surfer wishes to use surf tourniquet 1 for surfboard retention and the surfer has attached one end of a surfboard leash to a surfboard (not shown) to be retained by the leash. The user attaches the other end of the leash cord to surf tourniquet 1 via the cord attachment 25 of cuff body (unless the leash is already permanently attached).

The surfer places surf tourniquet 1, with sleeve 23 and body inner wall 16 facing the ankle, against the users skin. Grasping cuff body first end 12 and buckle 7, the user pulls the cuff band tight around ankle 100 and fastens cuff body first and second ends 12, 13 together using hook and loop fasteners 3, 4 to thereby form a closed loop around the ankle (see FIG. 3). As a result, sleeve 23 is disposed on the inside of the loop encircling ankle 100 and providing storage space and substantially 360 degree cushioning, while windlass bar 7 is stored in bar holder 8 on the outside of the loop on cuff body outer wall 17 and tourniquet strap 6 remains relaxed. The user tugs on the leash attached to cuff body 5 to check secureness, and, if necessary, adjusts the hook and loop fastener on cuff body first and second ends to adjust the size of the loop. The surf tourniquet functions as a surfboard cuff band for retaining the surfboard via the leash to the ankle of the surfer while surfing and without any obstruction from the tourniquet assembly.

Tourniquet Operating Configuration—Emergency

During an emergency situation the surf tourniquet is used to occlude massive bleeding from a limb for example, as a result of a limb of a surfer or other person being wounded by a shark attack. Initially, let us assume surf tourniquet 1 is operating in the surfboard retention configuration and is closed around the ankle of the surfer as shown in FIG. 3. In order to utilize surf tourniquet 1 as a tourniquet device, a user (which may be the surfer or another person) initially has to change the configuration of the surf tourniquet 1 from the surfboard retention operating configuration to a tourniquet operating configuration. To this end, a user manually opens the hook and loop fastener 3, 4 to detach the cuff body first and second ends 12, 13 from each other and removes surf tourniquet 1 from ankle 100. Grasping with one hand part of the tourniquet cuff protruding from sleeve opening 24, the user pulls the stored tourniquet cuff extension portion 9 completely out of sleeve 23 such that the tourniquet cuff and strap therein are free to extend laterally beyond the surfboard leash cuff body, as shown for example in FIGS. 4 and 5. The user then places surf tourniquet 1, with the inner wall of tourniquet cuff 10 facing the bleeding limb 200, against the user's skin and above the wounded limb area. Grasping cuff band body first end 12 and buckle 7, the user pulls tourniquet cuff 10 around the limb and feeds distal end 14 of cuff extension portion 9, including tourniquet strap portion 6A therein, through buckle 7 to close tourniquet cuff 10 and strap 6 in a loop around the limb and above the wound.

Preparatory to tightening of tourniquet strap 6 using windless bar 7, the user further pulls cuff extension 9 through buckle 9 to coarsely tighten the tourniquet cuff loop around the limb and then secures cuff extension 9 back onto tourniquet cuff 10 by mating together hook and loop fasteners 27,28 on the cuff outer wall. With surf tourniquet 1 now in an emergency closed position as shown for example in FIG. 6, the user releases windlass bar 7 from bar holder 8. The user then twists bar 7 about the rotational axis generally perpendicular to the longitudinal axis of strap 6 to twist the strap 6 on itself and incrementally further tighten the strap loop around the limb. Further tightening the loop around the limb reduces the circumference of the strap loop to thereby increase circumferential pressure around the limb and occlude blood flow from the wound. Continuing to rotate the bar further tightens the strap, increasing the circumferential pressure, while rotating in the bar in the opposite direction loosens the strap, decreasing the circumferential pressure.

Figure 6:
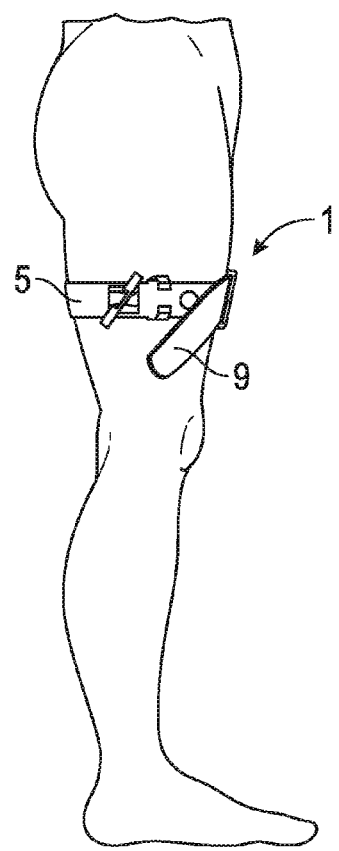
FIG. 6 is a side view of the outer side of the surfboard accessory in use as an emergency tourniquet device in which the accessory as configured in FIGS. 4 & 5 has been placed and tightened in a loop around the thigh of a patient and is in an a emergency closed configuration.
Figure 7:
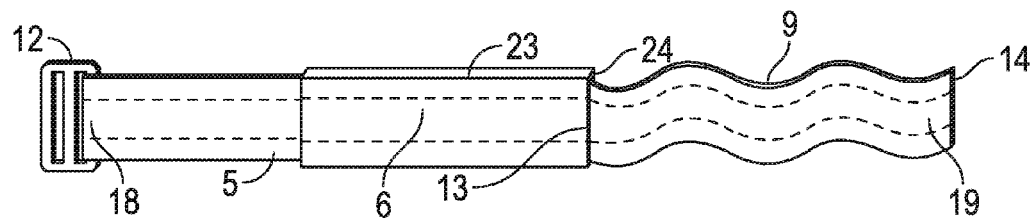
FIG. 7 is an outer side view of the surfboard accessory of FIG. 1 in the tourniquet operating configuration.
Figure 8:
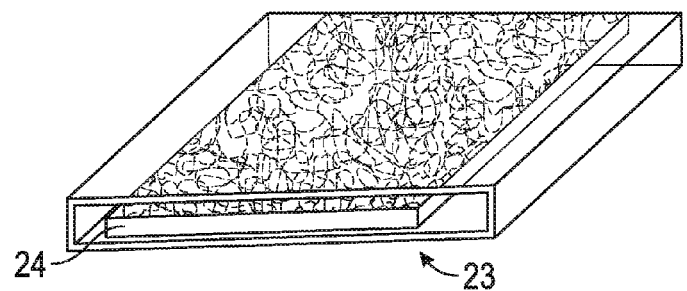
FIGS. 8 & 9 are perspective, isolated views of an exemplary storage component and windlass bar locking mechanism, respectively, of the surfboard accessory according to one embodiment.
Figure 9:
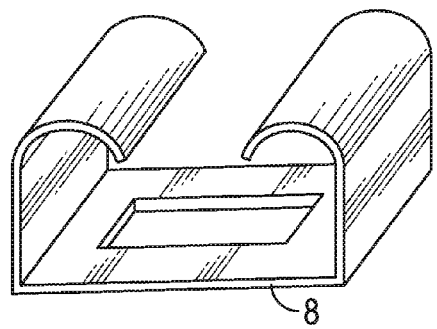
Figure 11:
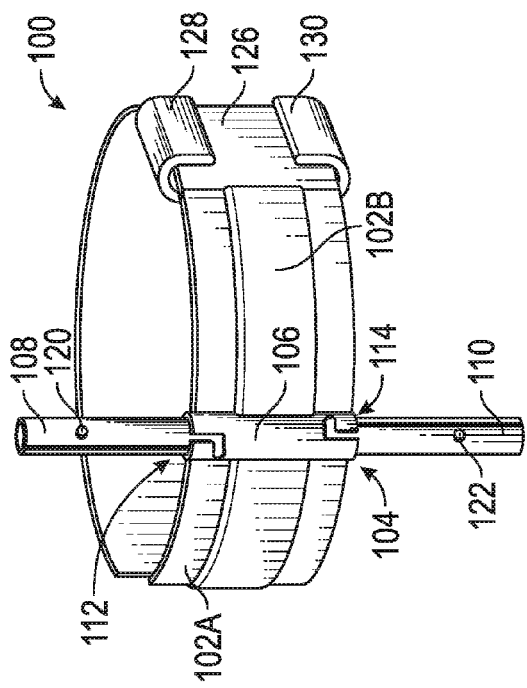
FIG. 11 is a perspective view of the tourniquet device with handles in an extended position.
Figure 13:
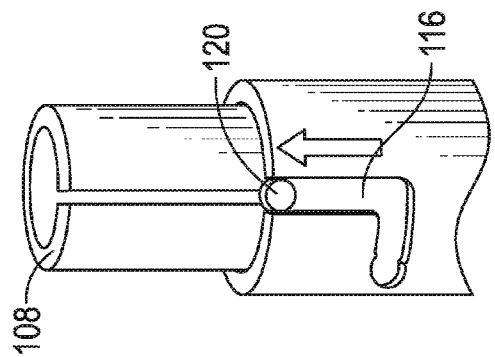
FIG. 13 is a perspective view of a handle of the tourniquet device of FIGS. 10 and 11 in an unlocked configuration.
Figure 10:
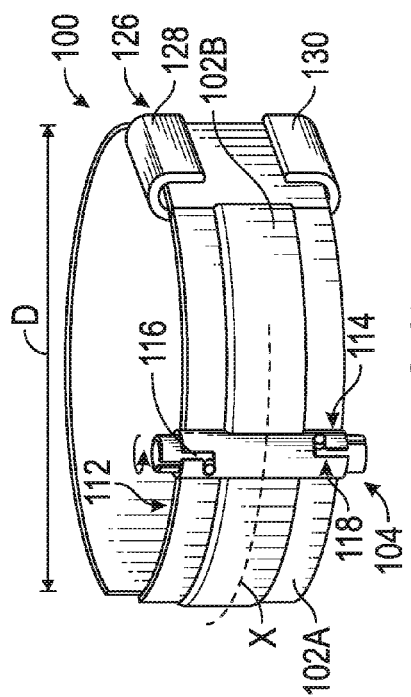
FIG. 10 is a perspective view of a tourniquet device, constructed in accordance with another embodiment of the present technology.
Figure 12:
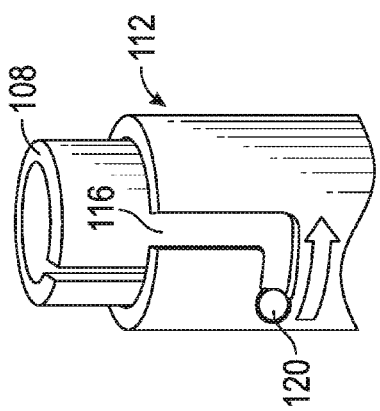
FIG. 12 is a perspective view of a handle of the tourniquet device of FIGS. 10 and 11 in a locked configuration.

Once the user has adjusted the tourniquet strap tension to achieve the desired circumferential pressure and prevent massive bleeding from the wound, the user places windlass bar 7 into the bar holder 9 to store the bar and lock in the set amount of circumferential pressure, as shown for example in FIG. 6. If necessary, windlass bar 7 can then be removed from bar holder 8 and slowly released or further tightened, as needed.

Methods of operation of the surf tourniquets of the aforementioned alternative or additional embodiments are similar, where appropriate, to the method of operation of the surf tourniquet 1 described above.

A method of manufacturing a surf tourniquet will now be described with reference to the accompany drawings. Tourniquet strap 6 may be formed from a seamless sheet or cord of nylon or other material. Surfboard cuff band body 5 and lateral cuff extension portion 9 may be formed from a continuous strip or sheet of nylon or other material. When folded along the central longitudinal axis, a pair of longitudinal adjacent first and second panels of the sheet is provided. The first panel is the inner wall material of the tourniquet cuff 10, that is, the inner wall of both the cuff band body 5 and lateral cuff extension portion 9. The second panel is the outer wall material of the tourniquet cuff 10, that is, the outer wall of both the cuff band body 5 and lateral cuff extension portion 9. The perimeter of the panels is cut to the required profile of the inner and outer walls either before or after they are folded together. Prior to folding the sheet panels closed together to form cuff band body 5 and lateral extension member 9, opening 20 is cut in the second sheet panel that will serve as cuff body outer wall 17.

Windless bar 7 is threaded onto tourniquet strap 5 and the strap is placed longitudinally along the length of the inner side of the second sheet panel that is to be folded onto the first panel. Strap 5 is placed so as to bridge the opening 20 with strap first end 18 extending beyond opening 20 and located at the end of the second panel and windlass bar 7 pushed through opening 20. The hole or section may not necessarily be cut in the strap for the internal strap to connect with the windlass bar. It may stop short leaving an area where the webbing is not folded over into two parts, but one, and then after the windlass bar and securing holder said webbing may restart. In one example, rather than cutting an opening 20, the second panel may already have an open area such that when the panels are folded closed together the second panel open area leaves a corresponding part of the first panel uncovered and serves as opening 20.

Opposite ends 18, 19 of the strap are stitched to opposite ends of the second sheet panel. The pair of sheet panels are then stitched or seamed together along the longitudinal edges, using suitable thread, leaving a sufficiently hollow interior between the two panels such that strap portion between the fixed opposite ends 18, 19 is disposed longitudinally between the panels and free to move.

Buckle 7 is attached to cuff body first end 12 using stitched material such as a nylon material. The storage sleeve is formed from two sheets of webbing material or other material that are stitched together along the longitudinal sides and at one end leaving the opening at the opposite end. The longitudinal edges and closed end sewn together. A neoprene or other cushion backing material is stitched along the inner wall of sleeve 23. The resulting sleeve 23 is then stitched to inner wall 16 of cuff band body 5 to carry sleeve on the cuff body.

The aforementioned method of manufacture is just one of many different ways to manufacture surf tourniquet 1. Methods of manufacture of the surf tourniquets of the aforementioned alternative or additional embodiments are similar, where appropriate, to the method of manufacturing of the surf tourniquet 1 described above. For example, other aspects including additional embodiments are described below with reference to FIGS. 10-42. The embodiments described in FIGS. 10-42 can be used universally to create pressure on an appendage above a cut, abrasion, or other injury where excessive blood loss can occur. The devices can be worn as bracelets, anklets, or can be worn around any body part. The devices can be used in any injury situation occurring during hiking, running, a sporting event, hunting, or any other occasion where injuries may occur and emergency personnel may be remote. The present technology can be used in battlefield or military scenarios where individuals may have need for tourniquet. The devices of the present technology can be worn around an appendage or stored on the individual until the tourniquet needs to be deployed and used. Thus, the devices of the present technology need not include an interface for a leash or tether, although some embodiments provided herein include such interfaces.

In general, the embodiments of FIGS. 10-30 include similar body portions but each of the devices can include a unique windlass device and/or windlass securement device. Furthermore, individual components of windlass devices can be exchanged or combined as desired. In some embodiments, multiple windlass devices can be used on the same tourniquet device, providing back up or redundancy if one windlass device fails.

Referring now to FIGS. 10-13, a tourniquet device 100 is illustrated according to another embodiment. The tourniquet device 100 comprises a first strip of material (body) 102A that can be fabricated from a mesh or nylon material, in some embodiments. The first strip of material 102A can be fabricated from any material or combination of materials such as leather, a textile, a resilient material such as a rubber, or other similar materials. The first strip of material 102A has a longitudinal axis X.

A second strip of material 102B overlays the first strip of material 102A and extends along the longitudinal axis X. The second strip of material 102B can also be fabricated from any one or a number of materials, similarly to the first strip of material 102A.

The device 100 comprises a windlass device 104 that generally comprises a tubular housing 106 and a pair of handles 108 and 110. The windlass device 104 is coupled with the second strip of material 102B. In one embodiment, the second strip of material 102B is threaded or passed through the tubular housing 106.

The tubular housing 106 includes a first end 112 and a second end 114 that each comprise a locking channel such as locking channel 116 and locking channel 118.

The pair of handles 108 and 110 is each sized to insert within the tubular housing 106. In one embodiment, each of the pair of handles 108 and 110 includes a protrusion such as protrusion 120 and protrusion 122.

To lock the pair of handles 108 and 110 in the tubular housing 106, the pair of handles 108 and 110 are pushed towards one another, in alignment with the tubular housing 106. The protrusions 120 and 122 engage with the locking channel 116 and locking channel 118, respectively. Each of the pair of handles 108 and 110 is twisted until its protrusion comes to rest in a locking section of the locking channel. For example, protrusion 120 is locked into the locking section 124 of locking channel 116.

In one example, the locking channel 116 is narrowed proximate the locking section 124 to keep the protrusion 120 locked in the locking section 124 until sufficient torque is applied to the handle 108 by a user.

When the handle 108 is unlocked, the protrusion 120 is moved upwardly into the locking channel 116, allowing the handle 108 to be extended from the tubular housing 106.

In one embodiment, the handles 108 and 110 are resiliently biased with a spring between them, disposed inside the tubular housing 106. When the handles are unlocked the spring (not shown) moves the handles into an extended position (see FIG. 11).

A windlass securement member 126 is coupled to the device 100. The windlass securement member 126 comprises a substantially C-shaped bracket that includes a downturned clip 128 and an upturned clip 130.

In operation, the device 100 can be wrapped around an appendage of a user when an injury to the appendage has occurred. Prior to deployment, the windlass device 104 is kept in a stored configuration (FIG. 10), where handles 108 and 110 are in their locked configuration.

The windlass device 104 is moved into an extended position by unlocking one or more the handles 108 and 110 and extending them. Once deployed, the user winds the windlass device 104, which twists the second strip of material 120B, which causes a diameter D of the device 100 to reduce in size. As the diameter D of the device 100 reduces, it begins to exert compressive forces on the appendage. The user can continue to turn the windlass device 104 until bleeding ceases. To keep the windlass device 104 from unwinding, one of the handles 108 or 110 will engage with the either the downturned clip 128 or upturned clip 130. For example, the handle 108 is inserted in the space between the downturned clip 128 or upturned clip 130, lodging in either the downturned clip 128 or upturned clip 130, depending upon the direction in which the windlass device 104 will want to unwind.

Figure 16:
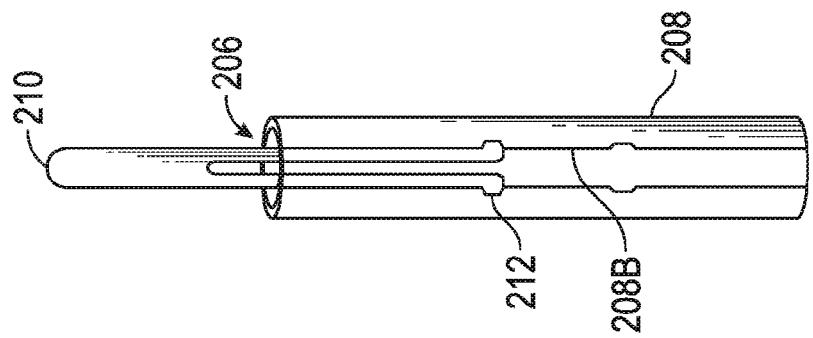
FIG. 16 is a cross sectional view of the handle being mated within a groove of the tubular housing.
Figure 15:
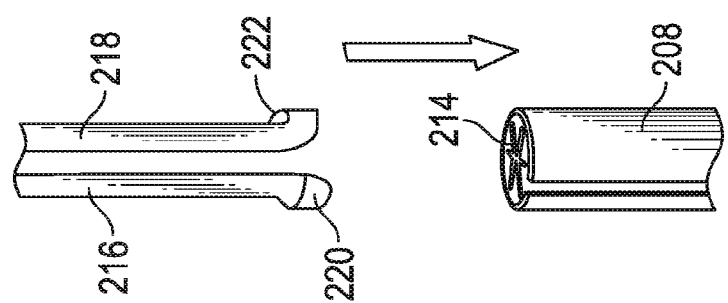
FIG. 15 is a perspective view of a handle being inserted into a tubular housing.
Figure 14:
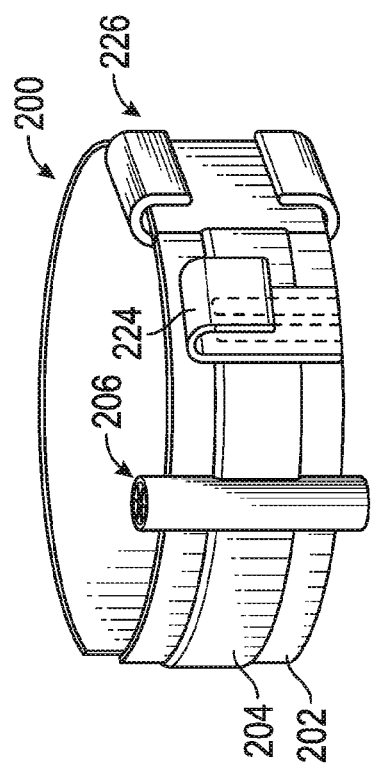
FIG. 14 is a perspective view of a tourniquet device, constructed in accordance with another embodiment of the present technology.

Referring now to FIGS. 14-16, a tourniquet device 200 is illustrated according to another embodiment. In this embodiment, the tourniquet device 200 also includes first and second strips of materials 202 and 204, respectively. The device 200 also comprises a windlass device 206 that comprises a tubular housing 208 and a handle 210 (also referred to as an "extension member"). The tubular housing 208 is coupled with the second strip of material 204 such that as the tubular housing 208 is wound the second strip of material 204 twists and tightens.

The tubular housing comprises an inner surface 208B that has a groove 212 fabricated therein. The groove 212 is designed to receive and retain a portion of the handle 210. In some embodiments, the tubular housing 208 comprises a grooved opening 214 (e.g., star shaped end). The tubular housing 208 is manufactured from a strong but resilient material such that an end of the handle 210 can be inserted into the groove opening 214, similarly to a straw that inserts into a lid opening.

In one embodiment, the handle 210 has a wishbone shape with two arms 216 and 218. The two arms 216 and 218 are spaced apart from one another. Each of the arms 216 and 218 is provided with a flared tip, such as flared tips 220 and 222, on a terminal end of the handle 210. The flared tips 220 and 222 are sized to fit into the groove 212 on the inner surface 208B of the tubular housing 208.

As the flared tips 220 and 222 are inserted into the tubular housing 208, the arms 216 and 218 are pushed towards one another. When the flared tips 220 and 222 encounter the groove 212, the arms 216 and 218, which are resiliently biased, will move away from one another to snap the flared tips 220 and 222 into the groove 212, thereby locking the handle 210 and the tubular housing 208.

According to some embodiments, the handle 210 can be stored in a pouch 224 that is attached to the device 100. As with the device 100 of FIGS. 10-13, the device 200 comprises a windlass securement member 226.

Figure 17:
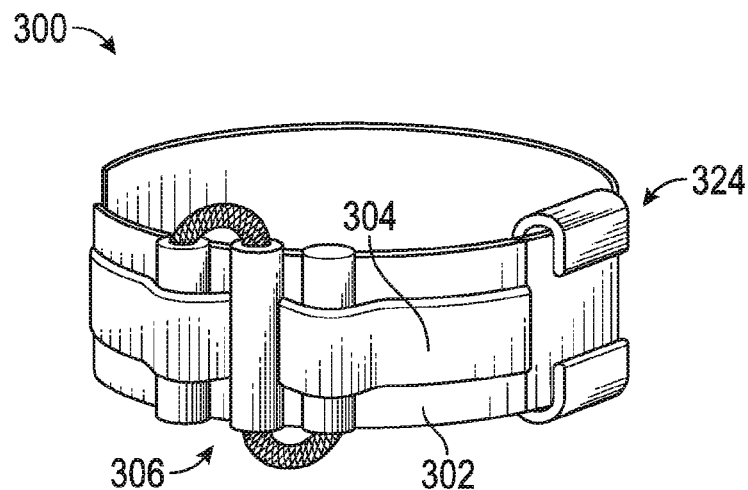
FIG. 17 is a perspective view of a tourniquet device with a corded handle windless device, constructed in accordance with another embodiment of the present technology.
Figure 18:
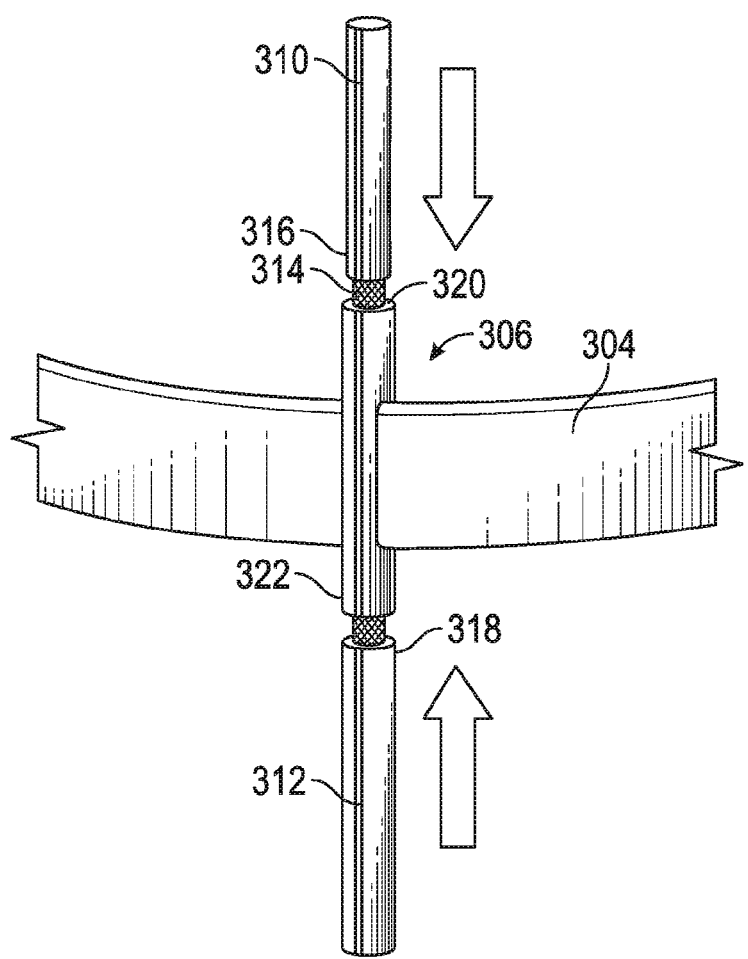
FIG. 18 illustrates the attachment of handles to opposing ends of a tubular housing.

Referring now to FIGS. 17 and 18, a tourniquet device 300 is illustrated according to another embodiment. Again, the device 300 comprises first and second strips of material 302 and 304. The device 300 also comprises a windlass device 306, which in this embodiment includes a tubular housing 308 and two handles 310 and 312.

Each of the handles 310 and 312 are associated with the tubular housing 308 by elastic cording. For example, handle 310 is associated with elastic cording 314.

The handles 310 and 312 are stored in between the first and second strips of material 302 and 304 when the tourniquet device 300 is not in use. When the device 300 is needed, the handles 310 and 312 are removed from storage between the first and second strips of material 302 and 304. The elastic cording is tensioned such that the handles 310 and 312 are pulled into linear alignment with the tubular housing 308. In some embodiments, terminal ends 316 and 318 of the handles 310 and 312 are configured to snap onto terminal ends 320 and 322 of the tubular housing 308 to create a continuous rod.

As with other embodiments, the device 300 comprises a windlass securement member 324 that engages with one of the handles 310 and 312 of the windlass device 306 to prevent the second strip of material 304 and the windlass device 306 from unwinding when the device 300 is in a cutoff position (e.g., compressed around an appendage of a user).

Figure 19:
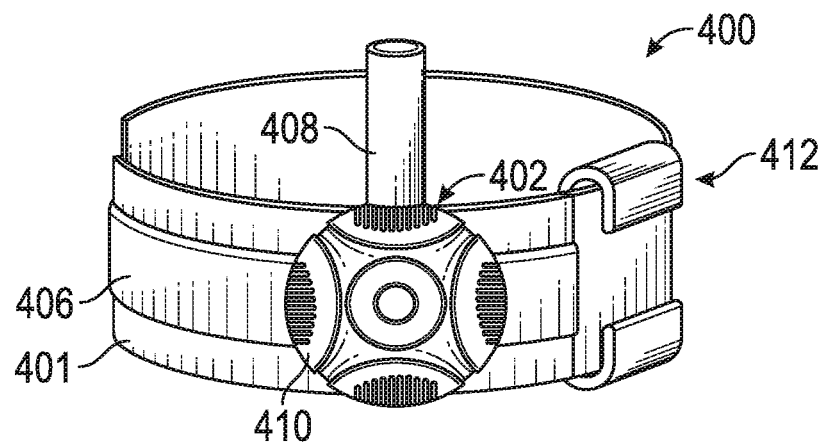
FIG. 19 is a perspective view of a tourniquet device with a dial windless device, constructed in accordance with another embodiment of the present technology.
Figure 20:
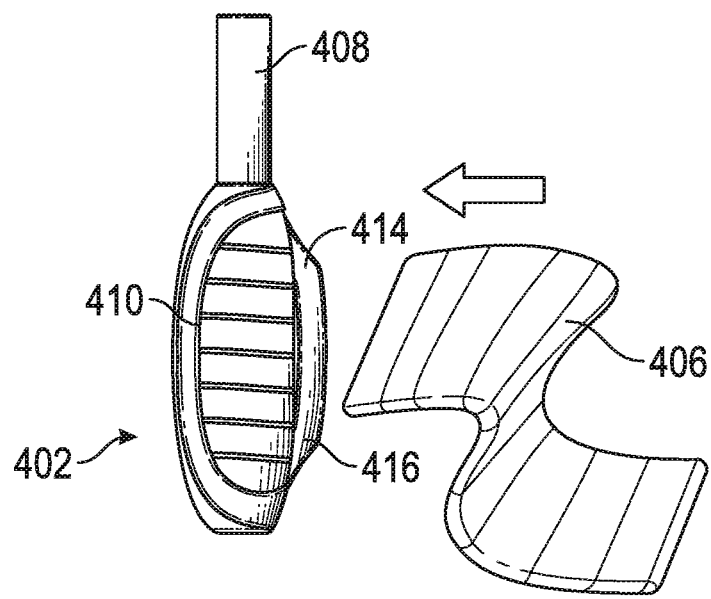
FIG. 20 is a side view of the dial windless device.

Referring now to FIGS. 19 and 20, a tourniquet device 400 having a dial windlass device 402 is shown according to another embodiment. The device 400 also comprises first and second strips of material 404 and 406, respectively.

The dial windlass device 402 is associated with the second strip of material 406. FIG. 20 illustrates the second strip of material 406 being threaded through a groove 414 formed by a bar 416 that is spaced apart from a back surface of the dial windlass device 402. The dial windlass device 402 also comprises a handle 408. The handle 408 can be used to wind the dial windlass device 402, which twists the second strip of material 406 that, in turn, reduces a diameter of the first strip of material 404.

The dial windlass device 402 includes a body 410 that can includes a rubberized coating that allows the dial windlass device 402 to be wound without requiring the handle 408.

The handle 408 is configured to engage with a windlass securement member 412 to prevent unwinding of the dial windlass device 402, as with other embodiments described above in FIGS. 10-18.

Figure 21:
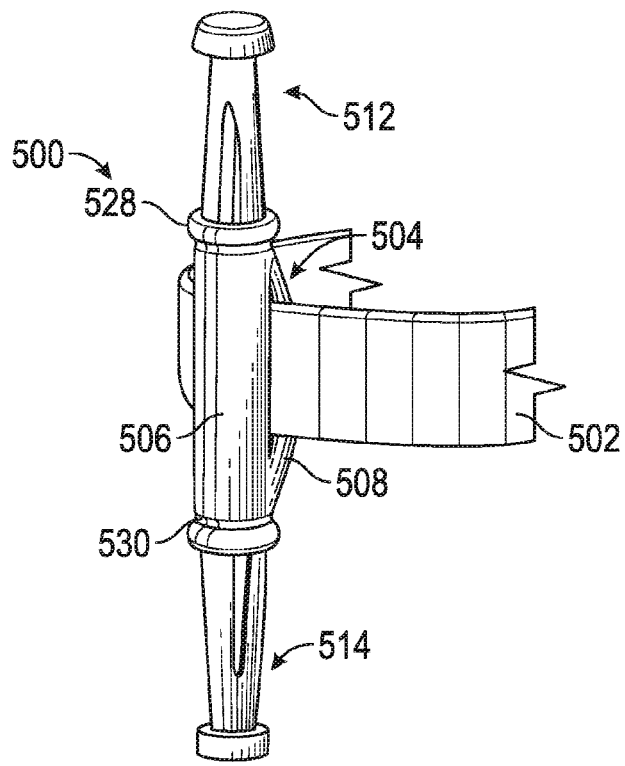
FIG. 21 is a perspective view of a tourniquet device with a wishbone handle windless device, constructed in accordance with another embodiment of the present technology.
Figure 22:
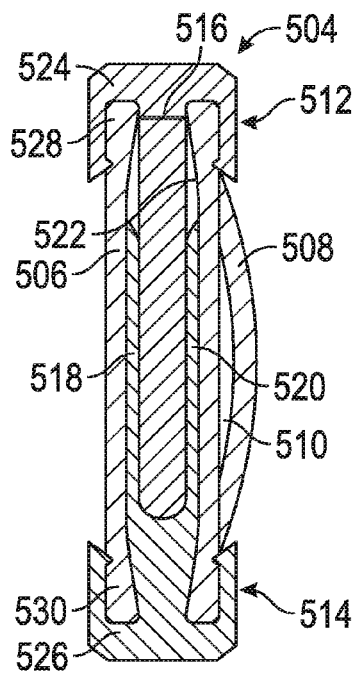
FIG. 22 is a cross sectional view of a pair of wishbone handles that are disposed in a locked configuration in a tubular housing.

Referring now to FIGS. 21-22, a tourniquet device 500 is illustrated according to another embodiment. The device 500 comprises a first strip of material 502 only. The device 500 also comprises a windlass device 504. The windlass device 504 comprises a tubular housing 506 that has a bar 508 extending so as to form a groove 510 that receives the first strip of material 502.

The windlass device 504 comprises a handle 512 and 514. In FIG. 22, the handle 512 is shown as comprising a T-shaped peg 516 and handle 514 is formed having a wishbone or pincher shape with arms 518 and 520. When the handles 512 and 514 are pushed together, the T-shaped peg 516 is inserted between the arms 518 and 520 of the handle 514. The arms 518 and 520 of the handle 514 are kept from expanding by the inner surface 522 of the tubular housing 506. Thus, the T-shaped peg 516 frictionally fits between the arms 518 and 520 of the handle 514.

Additionally, each of the handles 512 and 514 comprise a cap, such as cap 524 and 526, respectively. The caps 524 and 526 are each configured to snap over an open end of the tubular housing 506. For example, cap 524 snaps over an end 528 of the tubular housing 506 while cap 526 snaps over an end 530 of the tubular housing 506.

Figure 23:
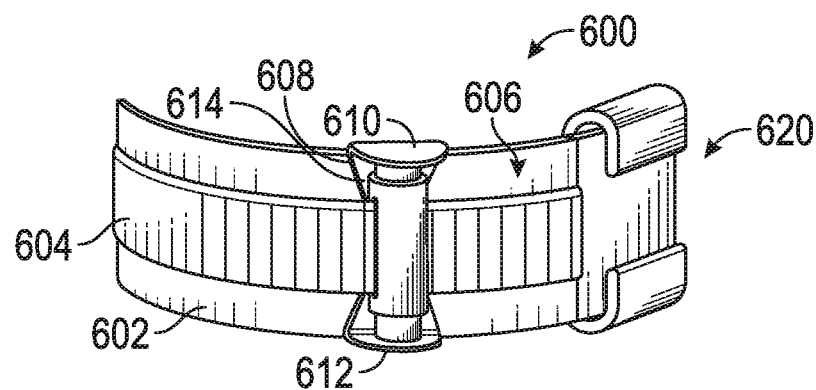
FIG. 23 is a perspective view of a tourniquet device with a windless device that has automatically extending handles and a clip for storing the handles, constructed in accordance with another embodiment the present technology.
Figure 24:
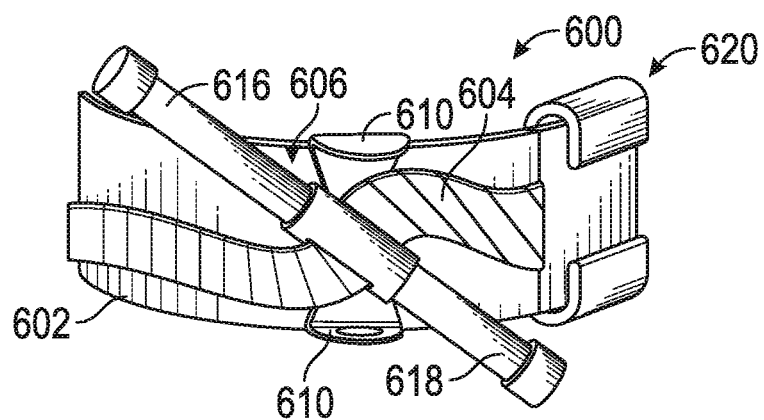
FIG. 24 is a perspective view of the windless device handles in an extended configuration.

Referring now to FIGS. 23 and 24, a tourniquet device 600 is illustrated according to another embodiment. The device 600 comprises first and second strips of material 602 and 604. The device 600 comprises a windlass device 606 that is associated with the second strip of material 604.

In some embodiments the windlass device 606 fits into a clip 608. The clip 608 includes support plates 610 and 612 that extend from a body 614.

In some embodiments, the windlass device 606 comprises a tubular housing 614 that receives handles 616 and 618. The handles 616 and 618 are resiliently biased to be in an extended position as shown in FIG. 24. To place the handles 616 and 618 in a storage position, the handles 616 and 618 are pressed into the tubular housing 614. The tubular housing 614 and handles 616 and 618 are placed into the clip 608 such that the ends of the handles 616 and 618 engage with the support plates 610 and 612, locking the windlass device 606 in the stored position.

To use the device 600, the tubular housing 614 and handles 616 and 618 are removed from the clip 608. Removal of the tubular housing 614 and handles 616 and 618 causes the handles to automatically and resiliently extend from the tubular housing 614 into an extended position. As with the other devices described above, the handles 616 and 618 can be used to turn the tubular housing 614, which in turn, twists the second strip of material 604. One of the handles 616 and 618 can be locked into a windlass securement member 620 as required.

Figure 25:
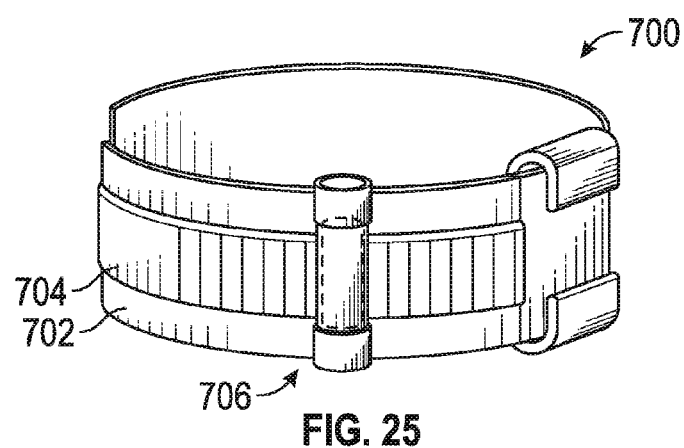
FIG. 25 is a perspective view of a tourniquet device with a windless device that comprises pin locks, constructed in accordance with another embodiment of the present technology.
Figure 26:
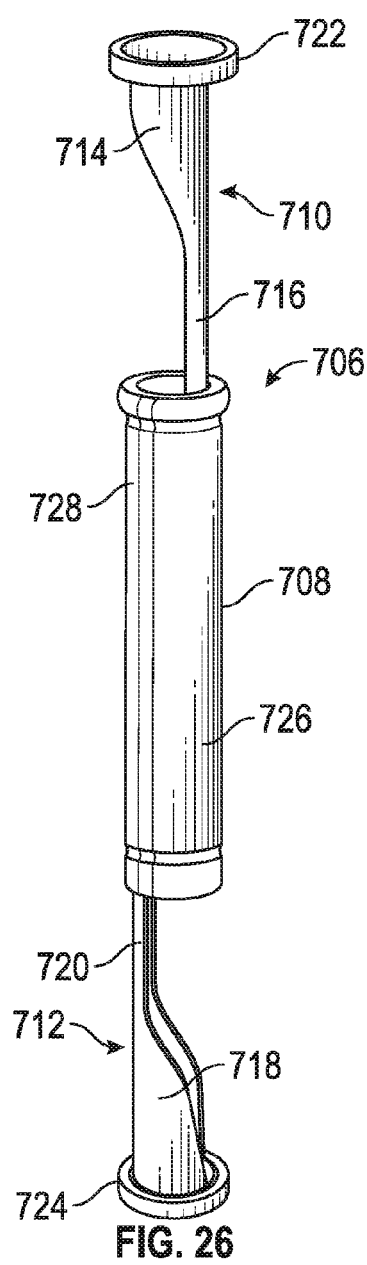
FIG. 26 illustrates the pin locks of FIG. 25 in an extended position.
Figure 27:
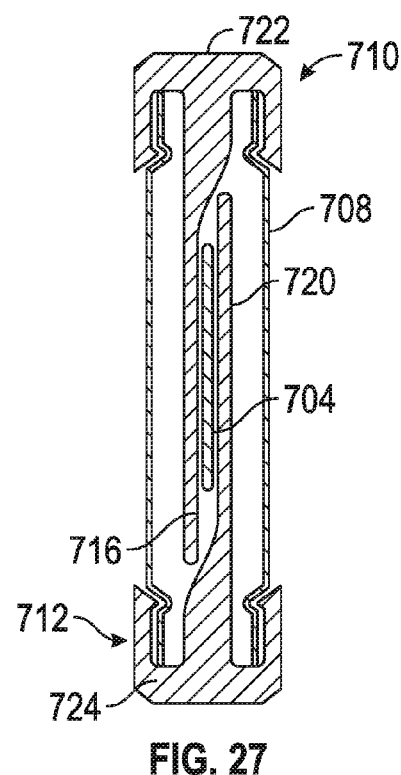
FIG. 27 illustrates the pin locks of FIGS. 24 and 25 in a locked configuration inside a tubular housing, the pins having caps that snap onto the open ends of the tubular housing.

Referring now to FIGS. 25-27, a tourniquet device 700 is illustrated according to another embodiment. The device 700 comprises first and second strips of material 702 and 704, as well as a windlass device 706 and windlass securement member 708. The windlass device 706 comprises a tubular housing 708 that receives two handles 710 and 712.

The handles 710 and 712 are shaped so as to mate within the tubular housing 708. For example, handle 710 is shaped such that it tapers from a larger end 714 down to a smaller end 716.

The handle 712 is shaped similarly to handle 710 as it has a larger end 718 and smaller end 720. When in use, the smaller ends 716 and 720 of the handles are turned in opposite directions, the handles are pressed into the tubular housing 708. The second strip of material 704 is disposed between the smaller ends 716 and 720 of the handles. As with other embodiments, the handles 710 and 712 each have a cap, such as cap 722 and 724 that cooperate with open ends of the tubular housing 708.

In one embodiment, the tubular housing 708 is comprised of a first section 726 and a second section 728. The first and second sections 726 and 728 can be separated from one another and put back together as desired.

Referring now to FIGS. 28-30, a tourniquet device 800 is illustrated according to another embodiment. The device 800 comprises first and second strips of material 802 and 804, as well as a windlass device 806 and windlass securement member 808.

The windlass device 806 comprises a slide rail handle 810 and a slide pin handle 812, as well as a cover 814. The windlass device 806 is coupled to the second strip of material 804. The slide rail handle 810 comprises a groove 816 that is configured to receive the slide pin handle 812.

In operation, the slide rail handle 810 and slide pin handle 812 can be moved to an extended position (FIG. 30). The handles can be used to wind the windlass device 806. When not in use, the slide pin handle 812 can be slid into the groove 816 of the slide rail handle 810 to bring the slide rail handle 810 and slide pin handle 812 together (FIG. 28).

Figure 31:
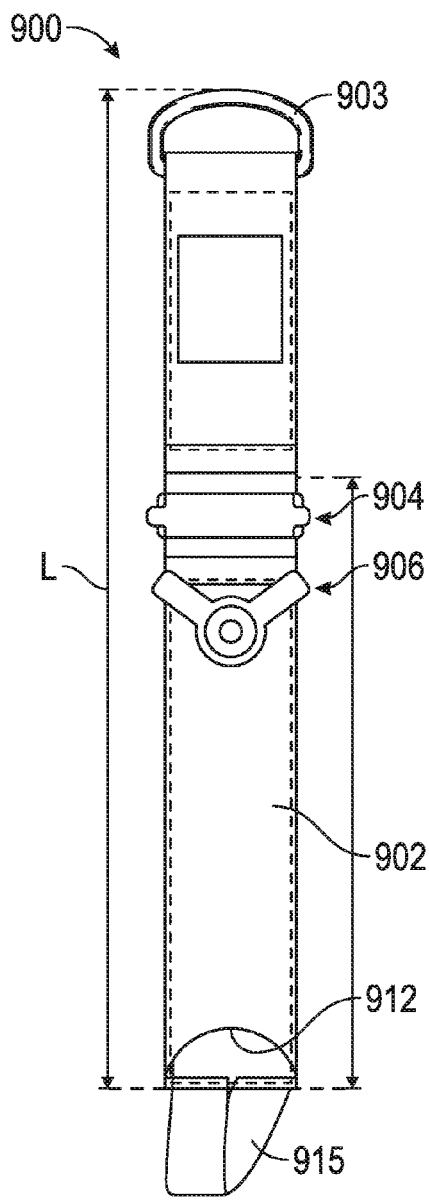
FIG. 31 is a front view of a tourniquet device with a windless device with pivoting arms, constructed in accordance with another embodiment of the present technology.

FIG. 31 illustrates another embodiment of the tourniquet device. The tourniquet device 900 comprises a belt 902, a buckle 903, a windlass device 904, and a windlass securement member 906.

Figure 33:
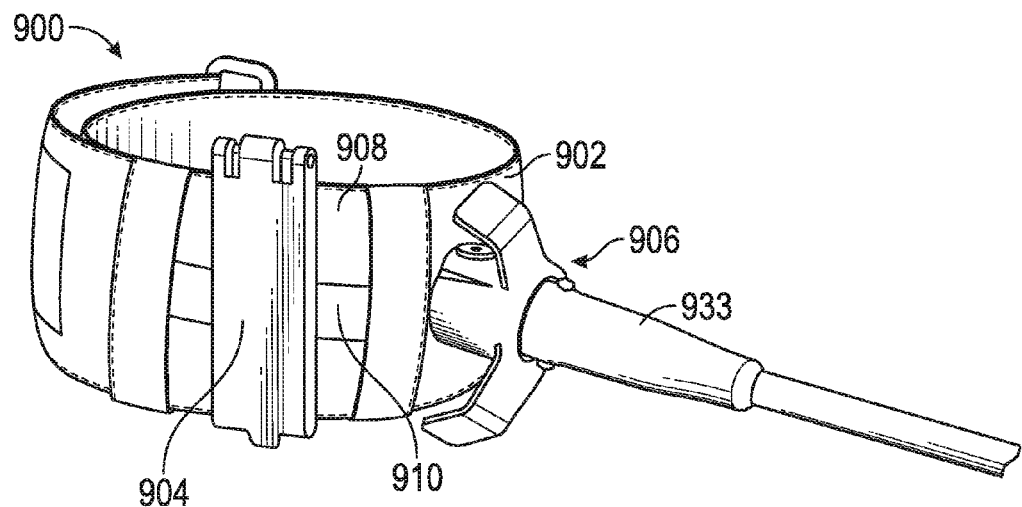
FIG. 33 is a perspective view of the device of FIGS. 31 and 32 showing a surf leash attached to a windless securement member.

The belt 902 is fabricated from any one or a number of materials such as a mesh, a fabric, a textile, a natural product such as leather or rubber, or any other suitable material. As illustrated in FIG. 33, the belt 902 is formed with an inside pocket 908 that receives a continuous strip of material 910. That is, the continuous strip of material 910 is housed within the belt 902. The continuous strip of material 910 is coupled to the windlass device 904.

In some embodiments, the continuous strip of material 910 is a strap of webbing material (or other elastomeric material) that is fed through the windlass device 904. The continuous strip of material 910 can be one strip of material that is sewn into one end of the belt 902 and looped around the buckle 903. In another embodiment, the continuous strip of material 910 is strip of webbing that is sewn into one end of the belt 902, looped around the buckle 903, and then the loose terminal end of the strip is sewn onto itself.

Turning back to FIG. 31, the belt 902 also comprises an external pocket 912. An extension portion 914 of the belt 902 is foldable and storable within the external pocket 912 to shorten the overall length L of the belt 902.

Figure 32:
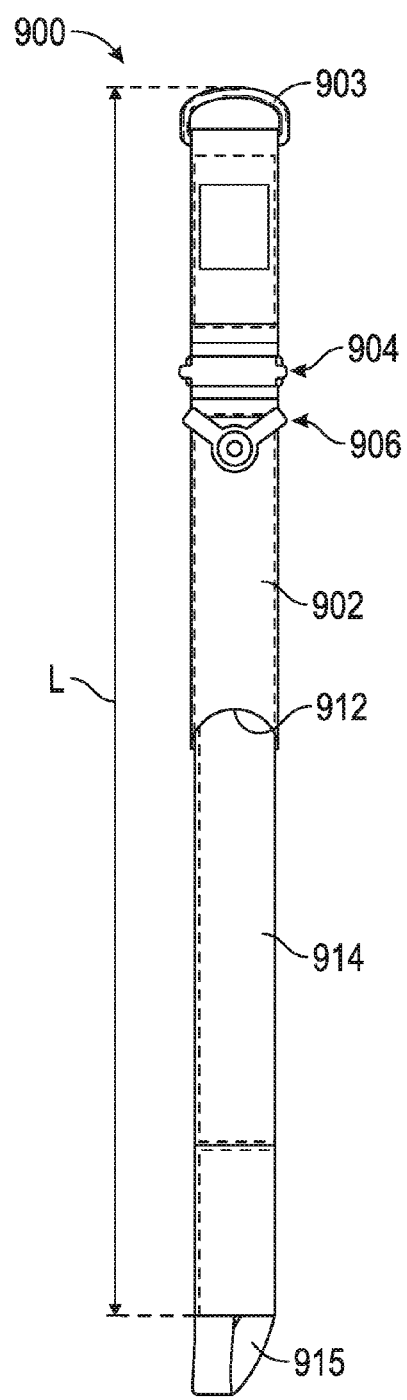
FIG. 32 is a front view of the tourniquet device of FIG. 31 in an extended position.

A deployment loop 914 is disposed on a terminal end of the belt 902 opposite the buckle 903. When the deployment loop 915 is pulled, the extension portion 915 is removed from the external pocket 912 which increases the overall length L of the belt 902 as illustrated in FIG. 32. Lengthening of the belt 902 may be advantageous when the device 900 is being used as a tourniquet for a larger extremity such as a thigh.

In some embodiments, the buckle 903 can be fabricated from a plastic, a polymer, a metal, an alloy, a resin, a natural material, or any suitable composite material.

Also, in some embodiments, the device 900 comprises a storage pocket 970 that is configured to store, for example, a car or house key. The pouch can also be configured to store credit cards, driver's licenses or other identification. The storage pocket 970 is fabricated from a section of webbing material that is sewn onto the belt 902. The storage pocket 970 can be sewn onto any portion of the belt 902 as desired.

Figure 34:
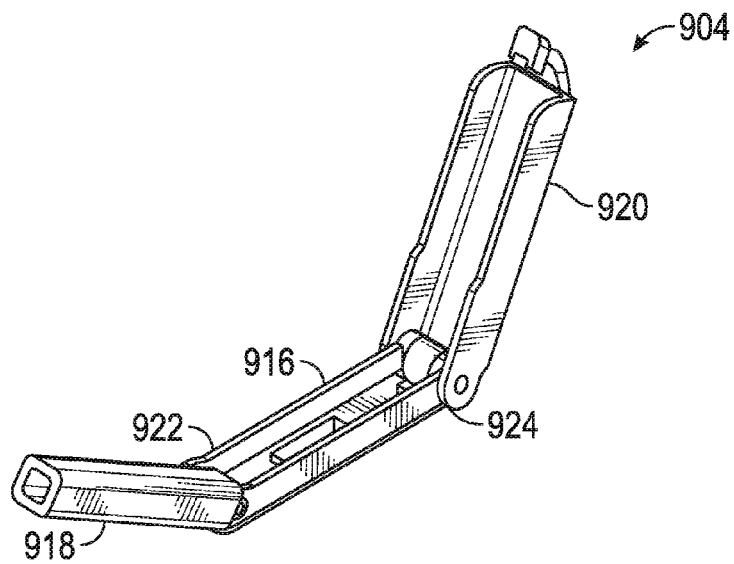
FIG. 34 is a perspective view of the windless device, illustrating an open position of the windless device where its arms are pivoted away from one another.
Figure 35:
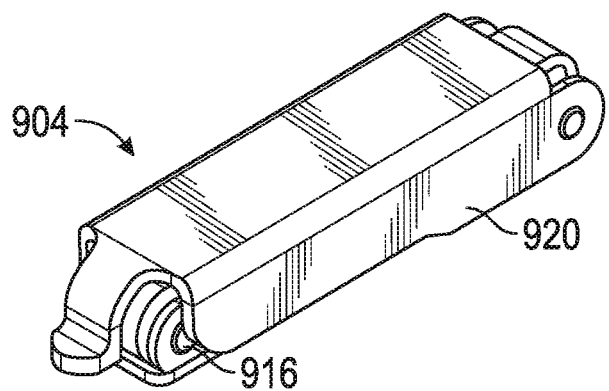
FIG. 35 is a perspective view of the windlass device in a stored configuration where the arms are folded and nested.

FIGS. 34 and 35 collectively illustrates the windlass device 904 that comprises a middle section 916, a first arm 918, and a second arm 920. In one embodiment, the middle section 916 is coupled to the continuous strip of material 910 (see FIG. 33) and the first arm 918 is pivotally connected to a first end 922 of the middle section 916. Also, the second arm 920 is pivotally connected to a second end 924 of the middle section 916.

The first arm 918 and the second arm 920 pivotally open in opposite directions from one another as shown in FIG. 35.

Additionally, the first arm 918 is configured to nest within the middle section 916 and the second arm 920 is configured to overlap and cover the middle section 916 when the first arm 918 is nested inside.

Figure 36:
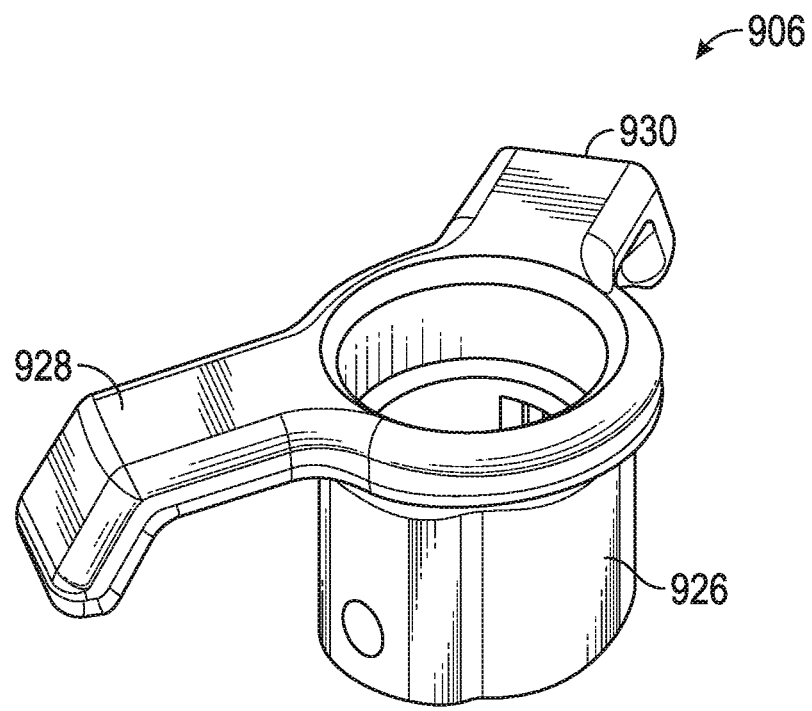
FIG. 36 is a perspective view of a windlass securement member.

Referring now to FIG. 36, the windlass securement member 906 comprises a hub section 926. The hub section 926 is joined to the belt 902 with a mounting plate (see 964 of FIG. 38) that is integrated into the belt material. The windlass securement member 906 includes hooks 928 and 930 that are each configured to serve as a point of engagement for securing the windlass device, as will be described in greater detail below.

The hub section 926 includes an interface 932 (see FIG. 37) that allows for connection with a surf leash 933 (see FIG. 33).

The hooks 928 and 930 have downturned ends in one embodiment. In another embodiment, the hooks 928 and 930 extend in different directions from one another.

Figure 37:
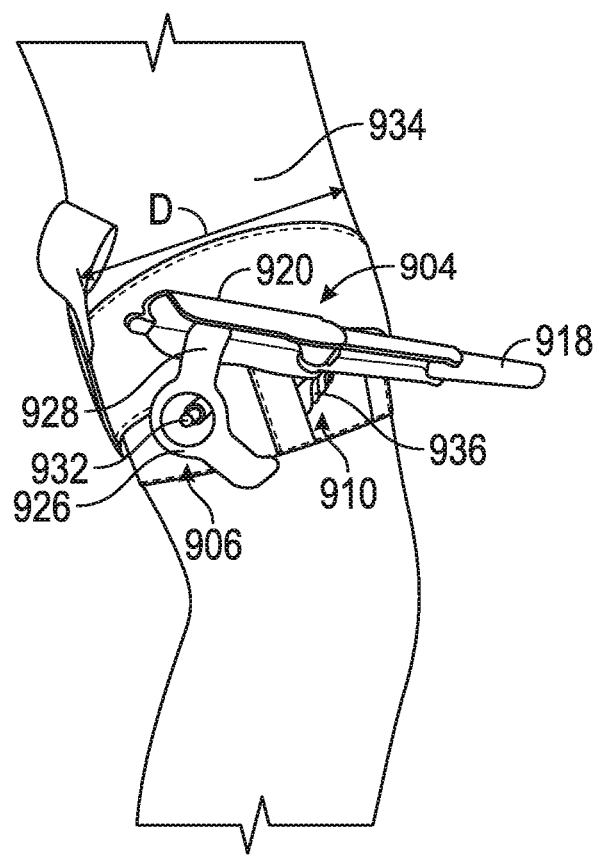
FIG. 37 is a perspective view of the device in operation around an appendage of a user, the windlass device being disposed in a locked configuration.

Referring now to FIG. 37, the device 900 is wrapped around the thigh 934 of a user. The windlass device 904 is illustrated in an extended position with first and second arms 918 and 920 deployed. The windlass device 904 has been used to twist 936 the continuous strip of material 910, which has reduced the diameter D of the device 900 to create a safe cutoff pressure in the thigh 934. To prevent the continuous strip of material 910 from unwinding, the second arm 920 is engaged with the hook 928 of the windlass securement member 906.

Figure 38:
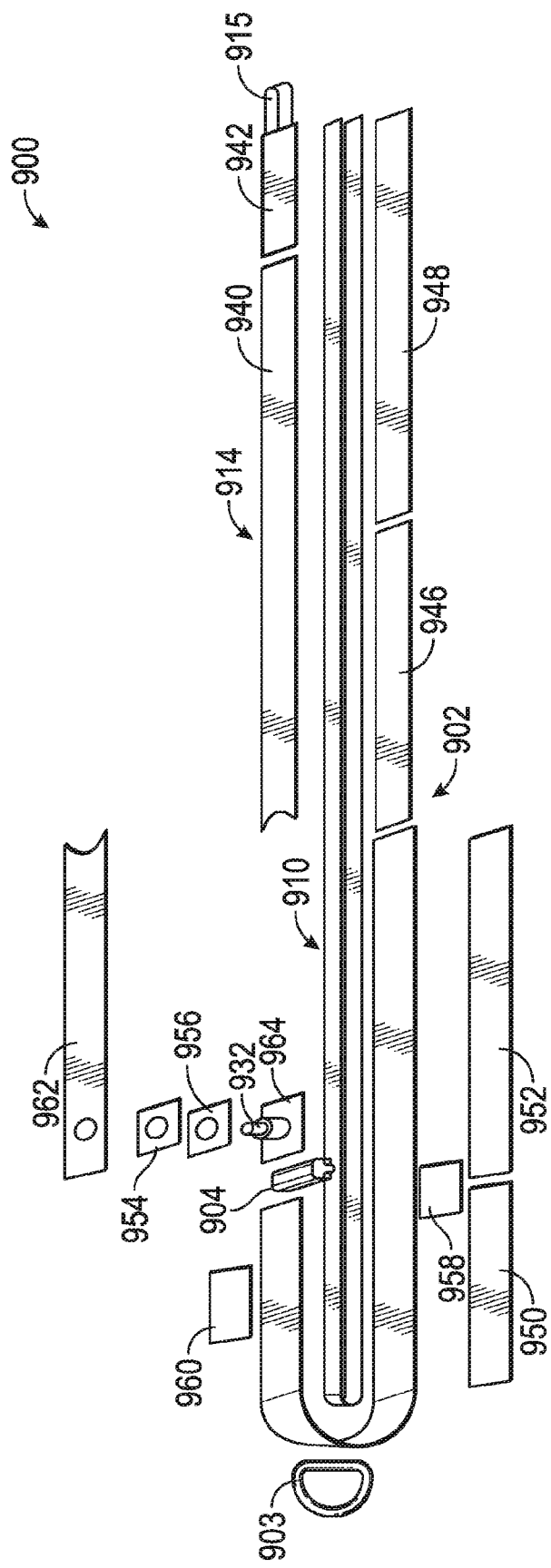
FIG. 38 is an exploded view of the tourniquet device of FIGS. 31-37.

Referring now to FIG. 38, an exploded view of the tourniquet device embodiment of FIGS. 31-37 is illustrated. The extension portion 914 is comprised of various sections of hook and loop material that can be overlapped before storage in the external pocket 912. For example, the extension portion 914 comprises a first section of loop material 940 that is coupled to a first section of hook material 942. The deployment loop 915 is coupled to the first section of hook material 942.

Attached to the belt 902 is a second section of loop material 946 as well as a strip of grosgrain (e.g., ribbed) material 948. The hook and loop sections can be overlapped for securement and the overlapped extension portion 914 can be stored in the external pocket 912.

Also, positioned on the rear of the belt 902 is a third loop section of material 950, which is also attached to a strip of lightweight neoprene material 952. Positioned between the third loop section of material 950, the lightweight neoprene material 952, and the belt 902 is a stiffener 958. The stiffener 958 is manufactured from ABS (acrylonitrile butadiene styrene), although other types of plastics or polymers can also likewise be utilized. The stiffener 958 will direct pressure downwardly and assist in occluding blood flow. For example, the stiffener 958 can direct the force of the windlass device 904 so as to tighten the lightweight neoprene material 952 onto the appendage.

The external pocket 912 is formed from an upper section of loop material 962 that is attached to the first section of loop material 940 of the extension portion 914. Positioned between the upper section of loop material 962 and the mounting plate 964 is a webbing section 954 and a nylon section 956. The interface 932 is joined to the mounting plate 964. Both the loop material 962 and the webbing section 954 have apertures that fit around the interface 932.

In one embodiment, the device 900 comprises an optional warning label and writing area 960 that is used to display instructions for proper use, as well as provide a user with a place onto which time information can be written. For example, a user can write onto the area 960 a time at which the device 900 was deployed and used to cutoff circulation to the desired appendage.

In some embodiments, the windlass device 904 can be covered with an optional section of webbing or elastic material 972 that protects the windlass device 904 when not in use and prevents the windlass device 904 from being inadvertently deployed. The material 972 can be attached with an adhesive or a lightweight stitching that can be easily torn. The material 972 can be selectively removed when access to the material 972 is needed.

In yet other embodiments, tourniquet 900 instead has a strap formed from double looped interior webbing attached to elastic. The windlass bar is configured to tighten webbing forming smaller closed loop until blood flow stops, and is then placeable in stopper.

The device of FIGS. 31-38 can be manufactured using the following method. In a first step, a user joins a ten inch by two inch neoprene piece of fabric (952) with a two inch wide section of loop material (950), end to end, using a three inch by one inch section of [Bailey Ribbon Mills "BRM"] webbing to create a clean finish. The user can stitch as close to the edge as possible while still keeping the sections securely connected with one another.

In a subsequent step, the user can assemble a front and back of a tourniquet housing by stitching, turning, and top-stitch Paiho ETB09 low profile loop (940) to Paiho ETN 32C low profile hook (942). The process is repeated with an eight and one half inch ETB09 (946) and a one and one-half inch wide section of Grosgrain (948). It will be understood that this grouping should be slightly longer than the top section because this will wrap around to create a clean finish at the end of tourniquet.

Next, the user stitches the backside of tourniquet material to the neoprene piece joined in the initial step above. The user can utilize a very small box stitch or multiple lines of stitches to secure this to the neoprene. The user can then stitch a BRM 7440 webbing (902) to the neoprene piece that was joined above, securing all four sides of neoprene and loop to form the pocket that receives the continuous strip of material 910.

An oval shape is cut in the top layer of tourniquet housing (940 and 942). The continuous strip of material 910 (e.g., tourniquet material) is inserted through the D-ring and windlass mechanism 904, and then the center fold is placed on the left side of the tourniquet. The user places both ends of the tourniquet material at far right end of tourniquet housing (the tourniquet material is doubled throughout the entirety of product). Next, the user sews the top layer of tourniquet housing down to the back layer taking care to not catch the tourniquet material (continuous strip of material 910) in the stitches. The user then pins at the end of tourniquet securing the front piece, tourniquet material, and back, which allows for adjustability of the length of tourniquet material in later steps.

The user can then place the surf-leash spindle or connector (interface 932) in place on tourniquet. The user places die cut 1000 Denier Nylon (956) over top, as well as small BRM 7440 2 webbing piece (954). These components are secured down with two long box stitches or bar-tacking. The user should be careful to not catch the tourniquet material in any stitches.

The user cuts an oval in the right side of the wide loop (962) and places an end cap of one inch wide BRM 7440 cut at three and three quarters length at its end to create a clean finish at the end of the loop. The user places the loop (962) over top of spindle (932) with corresponding hole cut out to register it in correct spot. The user sews the top and bottom of the loop to the webbing and neoprene to secure it down.

The user then weaves an end of two inch BRM 7440 webbing (910) through D-ring and marks the correct length to get gap desired for windlass to turn while in use as tourniquet. The user places an end cap of one inch BRM 7440 on end of the webbing and then places a warning label on the front side of the webbing (this has a space to record time of application of tourniquet). Next, the user folds webbing over the D-ring and stitches down the webbing and loop underneath. The user pulls the tourniquet material taut at the very far right side of tourniquet housing, and trims to needed length. The user turns the one and one half inch grosgrains section (942) over and top stitches through tourniquet material, front and back housings, and also a five eighth inch grosgrain material section (deployment loop 915).

The user then folds and stuffs the tourniquet housing into the two inch wide section of leash, referred to above as the pocket 912. Finally, the user places the V-shaped windlass stopper (windlass securement member 906) and inserts a pin therein for securement.

The above method is only an example method for fabricating the device 900 and it will be understood that other methods, combinations of components, or materials can also likewise be utilized in accordance with the present technology.

In some embodiments, the windlass securement member 906 can comprise a substantially C-shaped hook rather than a V-shaped component described above. The C-shaped hook can be configured similarly to the windlass securement members, such as the windlass securement member of FIGS. 10 and 11.

Figure 39:
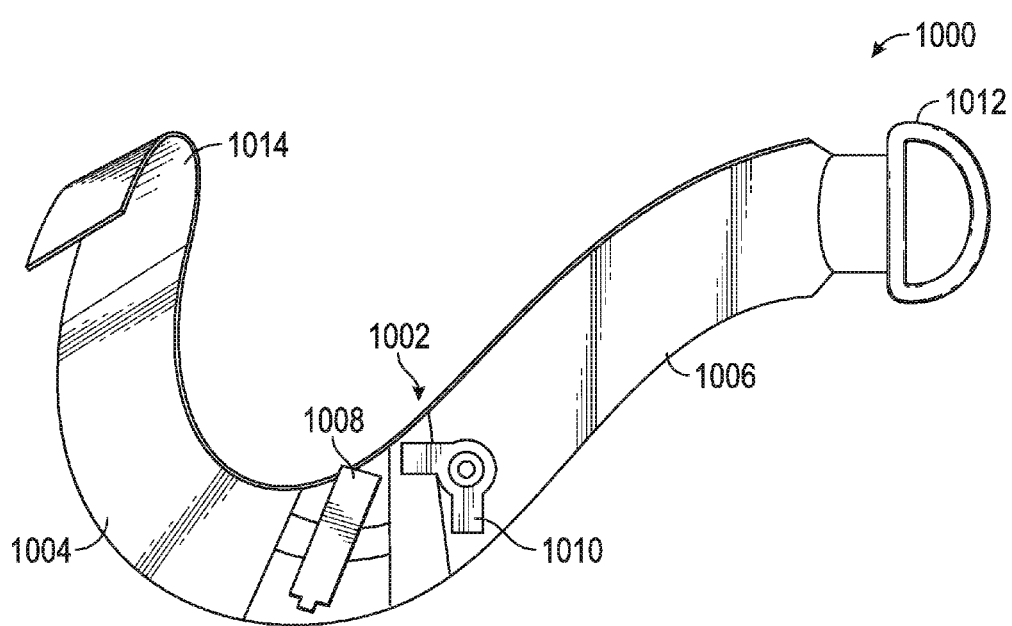
FIG. 39 illustrates a tourniquet device in a reverse configuration according to another embodiment.

FIG. 39 illustrates another tourniquet device 1000 according to another embodiment that is comprised of a belt 1002 that has an elastomeric portion 1004 coupled with a section of mesh or web material 1006. The device 1000 also comprises a windlass device 1008 and windlass securement device 1010 that are each similar to the windlass device and windlass securement device of FIGS. 31-38. A buckle 1012 is provided on one end of the belt 1002 and a section of hook material 1014 is disposed on the other end of the belt 1002. The hook material 1014 can be run through the buckle 1012 when the device 1000 is wrapped around an appendage of a user. The device 1000 can be initially cinched to the appendage by pulling the hook material 1014 through the buckle 1012 and joining the hook material 1014 to the outer surface of the belt 1002. That is, the outer surface of the belt 1002 can be provided with loop material or material that can cooperate with the hook material 1014 to facilitate the securement of the device 1000 around the appendage.

Figure 40:
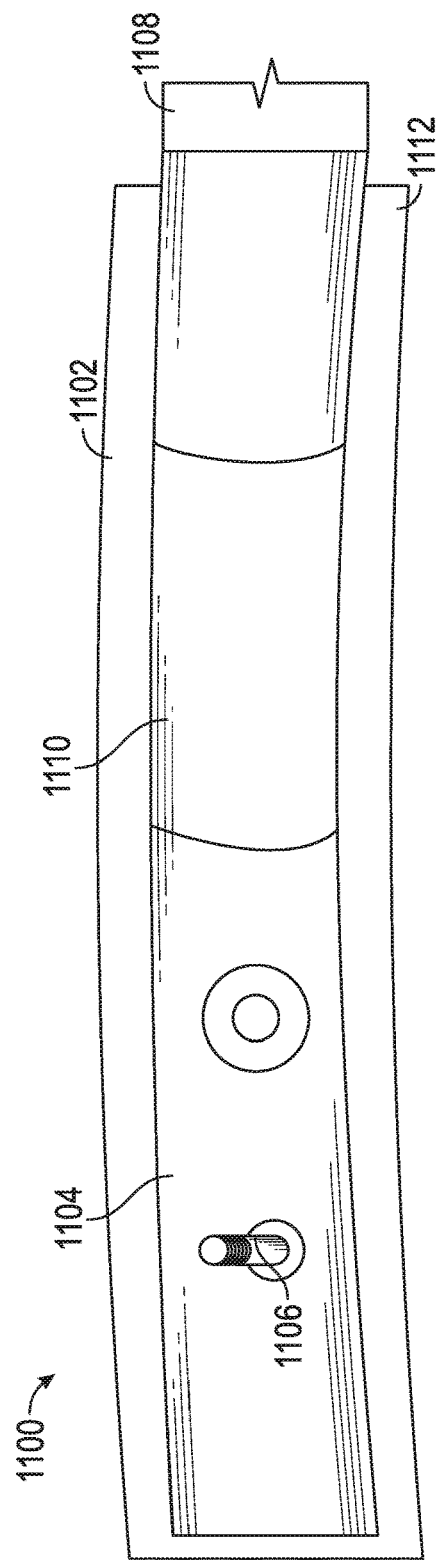
FIG. 40 illustrates a tourniquet device that utilizes pneumatic pressure according to yet another embodiment.

FIG. 40 illustrates a tourniquet device 1100 according to an embodiment that utilizes pneumatic pressure to occlude blood flow through an appendage. The device 1100 comprises a belt section 1102 that receives and retains an internal strap in the form of an inflatable tube 1104. The inflatable tube 1104 is coupled with a port 1106 that provides a path for inflating and/or deflating the inflatable tube 1104. The device 1100 also comprises an interface 1106 that is configured to couple with a surf leash, similarly to the components of the device 900 of FIGS. 31-38. The device 1100 also comprises a pull tab section 1108 where a portion of the belt section 1102 is stored prior to use. The user pulls the pull tab section 1108 to extend the belt section 1102, similarly to the device 900 illustrated in FIGS. 31 and 32.

In some embodiments, the inflatable tube 1104 can be disposed on an outer surface of the belt section 1102, rather than being disposed within the belt section 1102.

An end user can use a manual pump that is coupleable with the port 1106 to inflate the inflatable tube 1104, which causes pressure to be exerted on an appendage of a user, thereby occluding blood flow into the portion of the appendage below the device 1100.

In some embodiments, the inflatable tube 1104 is stored in a pocket 1110 that is formed into a portion 1112 of the belt section 1102.

While some of the components of the devices 900, 1000, and 1112 mention the use of neoprene, other similar synthetic rubber materials can also likewise be utilized in accordance with the present technology. Moreover, the materials stated herein are merely suggested materials and other materials can be substituted where appropriate.

Figure 41:
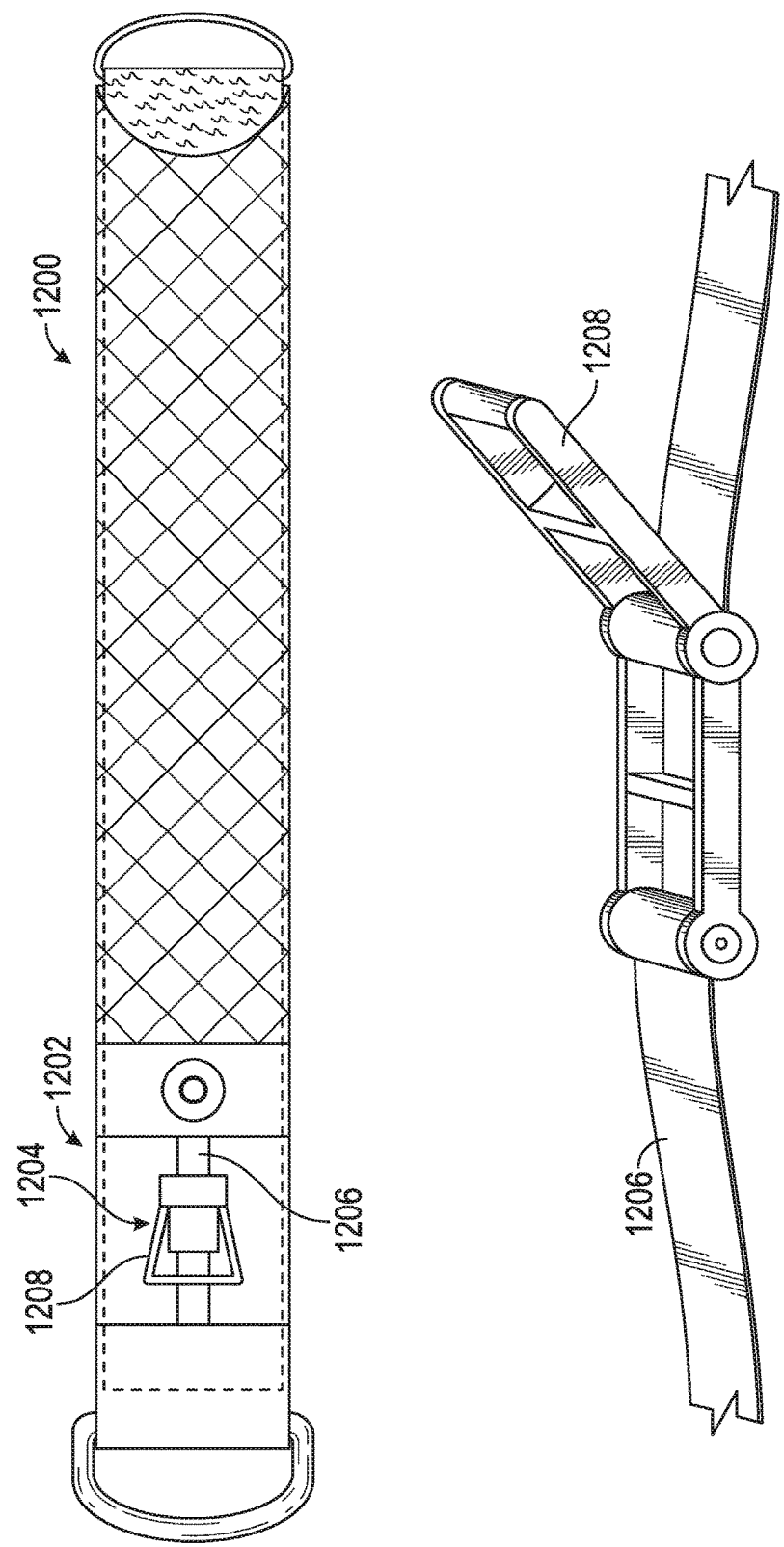
FIG. 41 illustrates a tourniquet device that utilizes a ratchet strap windlass device according to yet another embodiment.

FIG. 41 illustrates another tourniquet device 1200 according to yet another embodiment that comprises a windlass device 1202 that comprises a ratchet assembly 1204. The remainder of the device 1200 can be constructed similarly to that of the device of FIGS. 31-37. The ratchet strap 1206 includes a webbing strip that interfaces with a ratchet clasp 1208. In one example, the ratchet strap 1204 is a strip of webbing material that coils around the ratchet clasp 1208. As the ratchet clasp 1208 is actuated the ratchet strap 1206 is shortened in length to provide pressure to the appendage of the user. By way of non-limiting example the ratchet assembly 1204 functions similarly to a come-along device. It will be understood that the ratchet clasp 1208 acts as its own securement device when the ratchet clasp 1208 is folded down into a locked position. Thus, the device 1200 need not include a windlass securement device, although the use of a windlass securement device is not precluded and could be used as a backup or failsafe to ensure that the ratchet clasp 1208 does not unlock when the device has been deployed. In yet another embodiment, device 1200 is an elastic strap version with the ratchet for tightening. The elastic strap is configured to envelope the extremity. The ratchet can then be operated to tighten the strap around leg.

Figure 42:
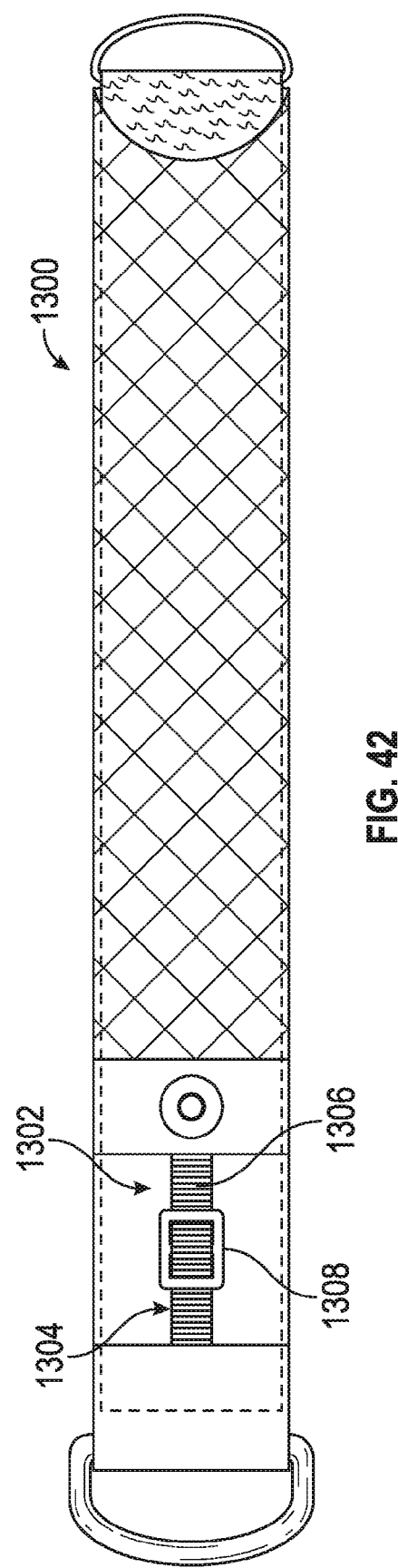
FIG. 42 illustrates a tourniquet device that utilizes another type of ratchet strap windlass device according to yet another embodiment.

FIG. 42 illustrates a tourniquet device 1300 according to yet another embodiment that comprises a windlass device 1302 that comprises a ratchet assembly 1304. The remainder of the device 1300 can be constructed similarly to that of the device of FIGS. 31-37. The ratchet strap 1306 includes a ribbed or grooved plastic strip that interfaces with a ratchet clasp 1308. As the ratchet clasp 1308 is moved laterally along the ratchet strap 1306, the overall length of the device 1300 can be lengthened or shortened as desired. Shortening of the device 1300 causes the device 1300 to apply pressure to an appendage. In yet another embodiment, device 1300 is an elastic version with a rigged plastic strip and corresponding ratchet for tightening. The elastic lets webbing wrap around limb. The ratchet uses mechanical advantage to move along track tightening strap.

Figure 47:
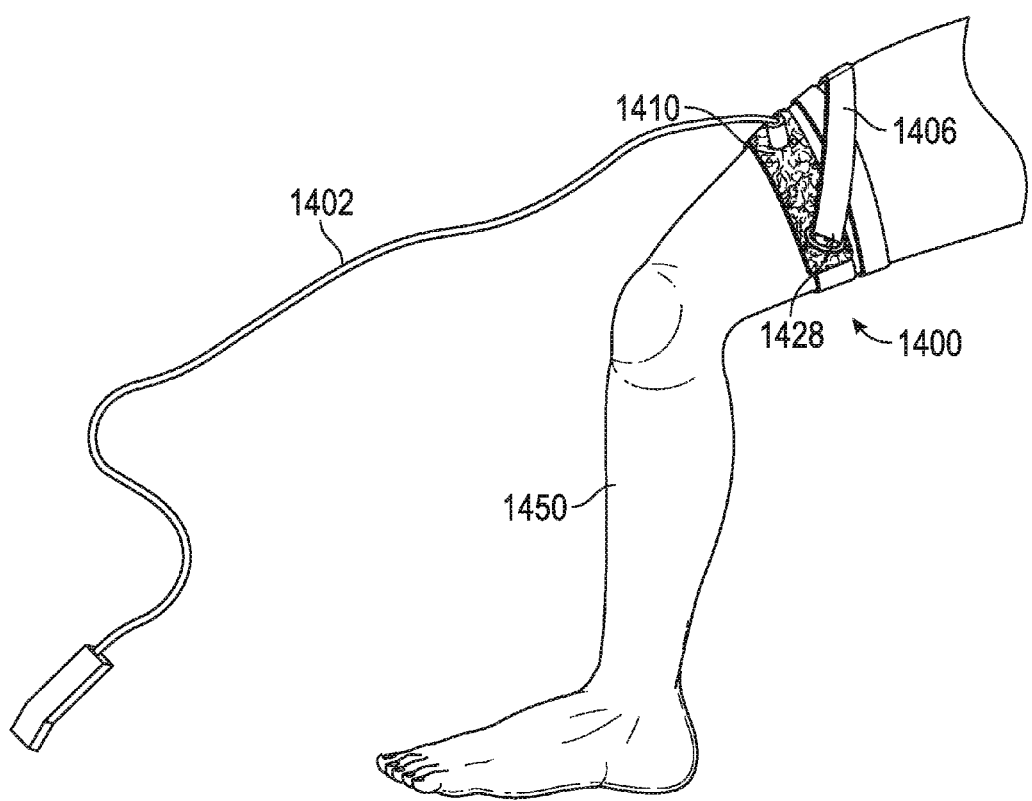
FIG. 47 is a perspective view of the tourniquet device of FIGS. 43-46 in use around and appendage of an individual to prevent blood loss from the appendage.
Figure 48:
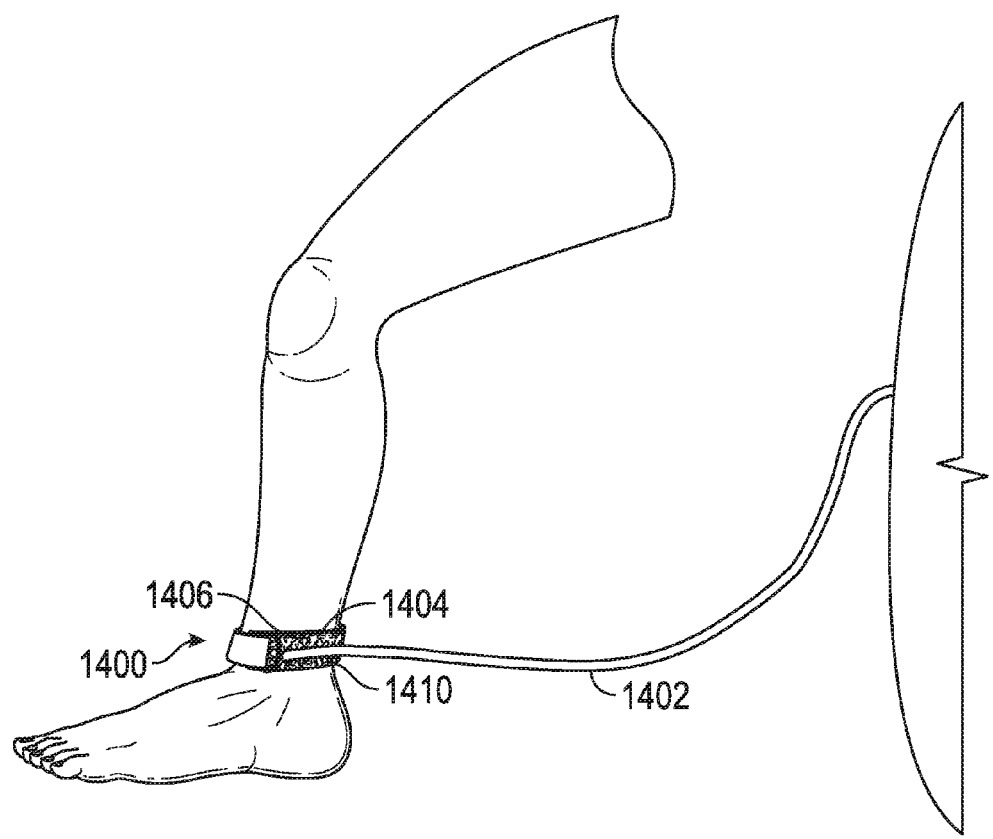
FIG. 48 is a perspective view of the tourniquet device of FIGS. 43-46 in use around and appendage of an individual in a wearable configuration.

In yet other aspects of the present technology, a kit of parts for assembling any one or more of the above described embodiments of the devices of FIGS. 1-48 is provided. The kit of parts comprises the described parts of the particular device and optionally a box or bag, and an instruction manual for assembling said device from said kit of parts; wherein said device parts and said instruction manual are carried in said box or bag. FIGS. 43-48 collectively illustrate an example tourniquet device 1400. The tourniquet device 1400 is illustrated in a stored position, referred to herein as a "wearable position". In the wearable position the tourniquet device 1400 can be wrapped around an ankle of an individual such that the tourniquet device 1400 can be used in combination with a surfboard leash 1402 as illustrated in FIGS. 47 and 48.

In some embodiments, the tourniquet device 1400 comprises a tourniquet strap 1404 that stores or hides a securement strap 1406 that can be deployed in the event of an injury to an appendage of an individual where the tourniquet device 1400 can be used to compress the appendage and reduce or prevent blood loss therefrom.

In some embodiments, the tourniquet strap 1404 is manufactured from an elastomeric material such as neoprene. In other embodiments, the tourniquet strap 1404 can be manufactured from a different material such as a textile or composite material. The tourniquet strap 1404 comprises an outward facing surface 1407 and an inward facing surface 1408. The outward facing surface 1407 is the portion of the tourniquet device 1400 that faces outwardly from the appendage when the tourniquet device 1400 is encircled around the appendage. The inward facing surface 1408 is the portion of the tourniquet device 1400 that contacts the appendage when the tourniquet device 1400 is encircled around the appendage.

In some embodiments, the outward facing surface 1407 is provided or covered, at least partially or entirely, with a plurality of hook fasteners 1410. For example, the plurality of hook fasteners 1410 are one half of a Velcro™ fastening system.

The tourniquet strap 1404 has a first end 1412 and a second end 1414 that are spaced apart from one another. In some embodiments, the plurality of hook fasteners 1410 are located proximate the first end 1412.

The first and second ends 1412 and 1414 are spaced apart from one another to define a first overall length L1. L1 is associated with the length of the tourniquet device 1400 in a stored position.

The tourniquet strap 1404 includes a buckle 1416 that is disposed on the first end 1412. The buckle 1416 can be created from any suitable material such as a plastic, polymer, metal, composite, or other suitable material that would be known to one of ordinary skill in the art with the present disclosure before them. Note that in some embodiments of tourniquet device 1400 and/or any of the other tourniquet device embodiments described herein, the buckle can be in the form of a loop of material, such as webbing, sewn or otherwise fixedly attached to or about the first end instead of fixed frame buckle 1416 or can be integrated in the first end itself i.e. a slot formed in the strap material itself.

According to some embodiments, the tourniquet device 1400 comprises an interface 1418 that can receive a surf leash (see FIG. 48). In another example, the interface 1418 can receive a pedestal such as the windlass securement member 906 illustrated in FIG. 36.

The second end 1414 is configured to form a cavity 1424 that stores the securement strap 1406 therein when the securement strap 1406 is in a stored configuration (as illustrated in FIGS. 43 and 44).

The securement strap 1406 is manufactured from an elastomeric material. The securement strap 1406 can be fixedly attached to the tourniquet strap 1404 inside the cavity 1424. In one embodiment the securement strap 1406 is sewn into the cavity along the line A.

The securement strap 1406 comprises a terminal end 1426. A pull tab 1428 is provided on the terminal end 1426 and can be used to extend the securement strap 1406 into a deployed configuration as illustrated in FIGS. 47 and 48 and described in greater detail below.

In FIG. 46, the inward facing surface 1408 is illustrated as being divided into a first section 1420 and a second section 1422. The first section 1420 is provide with a plurality of loop fasteners 1423 on its surface. The second section 1422 is a section of neoprene material (or other elastomeric material), which allows the tourniquet strap 1404 to stretch and accommodate the diameter of the appendage. Thus, the tourniquet strap 1404 can be used with any ankle size.

The plurality of loop fasteners 1423 engage with the plurality of hook fasteners 1410 on the outward facing surface 1407 to releasably secure the tourniquet device 1400 about the ankle of the individual when in the wearable position/configuration.

In FIGS. 45 and 46, the securement strap 1406 is illustrated in an extended configuration/position. A face 1430 of the securement strap 1406 is provided with a plurality of loop fasteners 1432. The plurality of loop fasteners 1432 join with the plurality of hook fasteners 1410 that are disposed on the outward facing surface 1407 of the tourniquet strap 1404.

When the securement strap 1406 is in the extended position, the tourniquet device 1400 has a second overall length L2. To be sure, the second overall length L2 is greater than the first overall length L1 when the tourniquet device 1400 is in the stored position/configuration.

To be sure, in some embodiments, the securement strap 1406 has a length that requires a portion of the securement strap 1406 to be folded or otherwise adapted to fit within the cavity of the tourniquet strap 1404. When the pull tab is 1428 is used to extend the securement strap 1406, the portion of the securement strap 1406 disposed in the cavity will unfold and increase the device to the second overall length L2.

In another embodiment, the tourniquet device 1400 is extended to the second overall length L2 by stretching the securement strap 1406 from its stored position to its extended position. Because the securement strap 1406 is attached to the inside of the cavity and the securement strap 1406 is made of an elastomeric material it will stretch to the extended position by pulling on the pull tab 1428. When the user releases the pull tab 1428 the securement strap 1406 will resiliently return to the stored configuration/position.

Turning now to FIG. 48, the tourniquet device 1400 is illustrated as being attached to an ankle of an individual (e.g., wearable configuration). In this embodiment, the tourniquet device 1400 is attached to the ankle by wrapping the tourniquet strap 1404 around the ankle and overlapping the plurality of loop fasteners 1432 (illustrated in FIGS. 45 and 46) on the inward facing surface 1408 onto the plurality of hook fasteners 1410 on the outward facing surface 1407. The deployment of hook fasteners 1410 on various parts (or all) the outward facing surface 1407 will function to allow the tourniquet device 1400 to accommodate ankles of varying size. As the size of the ankle increases the plurality of loop fasteners 1432 will trend towards attaching near an end of the plurality of hook fasteners 1410 on the outward facing surface 1407 (e.g., first end 1412). If the tourniquet device 1400 is not required to couple with a surf leash the plurality of loop fasteners 1432 on the inward facing surface 1408 can even overlap and cover the interface 1418.

Turning to FIGS. 43-48 collectively, when an appendage has been injured, the tourniquet strap 1400 can be used to selectively prevent blood flow to the injured appendage. In one embodiment, the tourniquet strap 1400 is detached from the ankle of the individual and the securement strap 1406 is deployed from within the tourniquet strap 1404 using the pull tab 1428. The tourniquet strap 1404 is positioned on the appendage a distance above the injury.

The pull tab 1428 is threaded through the buckle 1416 and the pull tab 1428 is pulled backwards in a direction of the inward facing surface 1408. The pull tab 1428 is used to wrap the securement strap 1406 around the appendage. With every successive loop of the securement strap 1406 around the appendage the tourniquet device 1400 tightens around the appendage cutting off blood flow to the area of injury 1450. When the desired level of compression has been achieved, the loop fasteners 1432 of the securement strap 1406 are attached to the plurality of hook fasteners 1410 on the outward facing surface 1408 of the tourniquet strap 1404.

Advantageously, the user can use the tourniquet device 1400 as a surfboard leash while surfing to retain their surfboard, and in the event of uncontrollable extremity bleeding can extend the stored tourniquet device 1400 a and use the same to stop bleeding of an appendage. To do so the user detaches the tourniquet strap 1404 from around the ankle, pulls the securement strap 1406 from the storage compartment, feeds the securement strap 1406 through the buckle on the opposite end of the tourniquet strap 1404 tightens the securement strap back towards the securement strap storage end and proceeds to wrap the securement strap as many times and as tight as possible around the appendage, and then secure the securement strap in place on the tourniquet strap.

In other embodiments, rather than utilizing complementary hook and loop fasteners, the tourniquet device 1400 can utilize buttons or snaps, as well as clips, buttons, and other securement means that would be known to one of ordinary skill in the art with the present disclosure before them. In yet other embodiments, tourniquet 1400 strap is formed from double looped interior webbing attached to elastic. The windlass bar is configured to tighten webbing forming smaller closed loop until blood flow stops, and is then placeable in stopper.

In yet another embodiment, the tourniquet device 1400 is an elastic strap version with webbing on non-sewn in end. Velcro is sewn into webbing piece and elastic is attached. All is folded and stored as normal in storage area. In yet other alternative embodiments, tourniquet devices are provided that include features of the embodiments of FIGS. 1-42 described hereinbefore. However, rather than utilizing tensioning devices, the tensioning devices are omitted and the complementary hook and loop fasteners, or alternative fasteners such as buttons or snaps, as well as clips, buttons, and other securement means that would be known to one of ordinary skill in the art with the present disclosure before them, are provided on the tourniquet device in a similar manner to the fasteners provided on the tourniquet device 1400 thereby enabling the tourniquet strap tightened around the appendage to be secured in place by the fasteners.

In yet other embodiments, a boogie board leash (also known as a body board leash) is coupled to the tourniquet device of the embodiments described and illustrated herein instead of the surf board leash.

While preferred embodiments of the present invention have been described and illustrated in detail, it is to be understood that many modifications can be made to the embodiments, and features can be interchanged between embodiments, without departing from the spirit of the invention.

The invention claimed is:

1. A surfboard accessory comprising:
   a hybrid surfboard leash tourniquet;
   wherein said hybrid surfboard leash tourniquet comprises
   a surfboard leash cuff band;
   a surfboard leash cuff band fastener carried on said surfboard leash cuff band for closing the cuff band in a loop around an ankle of a surfer;
   a surfboard leash cord attachment or interface configured to releaseably or permanently attach a surfboard leash cord to said surfboard leash cuff band; and
   a tourniquet strap tensioner; and
   wherein said tourniquet strap tensioner is carried on said surfboard leash cuff band in addition to said surfboard leash cuff band fastener.

2. The accessory of claim 1,
   wherein said hybrid surfboard leash tourniquet further comprises a tourniquet strap having a portion extendable laterally beyond the length of said surfboard leash cuff band to permit said tourniquet strap to be secured in a loop around a limb and tightened by said tourniquet strap tensioner to stop or control extremity blood flow in the limb.

3. The accessory of claim 2, further comprising a tourniquet strap storage component, carriable on said surfboard leash cuff band and arranged to removeably store at least a portion of said tourniquet strap such that the surfboard leash cuff band is closable around the ankle by the surfboard leash cuff band fastener without obstruction by said tourniquet strap.

4. The accessory of claim 3,
   wherein said tourniquet strap storage component comprises a pocket, sleeve, a clip, a fastener, a zipper storage closure, a flap storage closure or any combination thereof.

5. The accessory of claim 3, wherein said tourniquet strap storage component comprises a pocket or sleeve formed from a cushion material and extends sufficiently along the surfboard leash cuff band to substantially encircle, and provide cushioning to, the ankle when the surfboard leash cuff band is closed around said ankle of said surfer for surfboard retention.

6. The accessory of claim 3, wherein said surfboard leash cuff band, said tourniquet strap, surfboard leash cuff band fastener, and said tourniquet strap storage compartment, or any combination thereof is formed from a synthetic, natural rubber material, nylon, seat belt webbing or any combination thereof.

7. The accessory of claim 1, wherein said hybrid surfboard leash tourniquet is a one-handed self-applying tourniquet assembly.

8. The accessory of claim 1, wherein
   said hybrid surfboard leash tourniquet further comprises:
   a tourniquet strap having a first end fixed to a first end of the surfboard leash cuff band and wherein at least a portion of the tourniquet strap laterally extends from and beyond a second end of the surfboard leash cuff band, opposite the first end of the surfboard leach cuff band; and
   a tourniquet strap adjuster fixedly attached to or proximate said first end of the surfboard leash cuff band and engageable with said portion of said tourniquet strap for securing, and coarsely tightening, said tourniquet strap in a loop around said limb preparatory to tightening by said tourniquet strap tensioner.

9. The accessory of claim 8 wherein said surfboard leash cuff band has a hollow interior extending along a length of said surfboard leash cuff band and wherein said tourniquet strap extending from said first end of said tourniquet strap is freely housed inside said surfboard leash cuff band along said hollow interior such that the strap is movable by the tourniquet strap tension to adjust the circumference of the strap loop.

10. The accessory of claim 8, further comprising a tourniquet cuff comprising said surfboard leash cuff band and a lateral cuff extension portion extending laterally from the second end of the surfboard leash cuff band, wherein said tourniquet strap is longitudinally carried along the length of said tourniquet cuff and has a second end, opposite said first end of the tourniquet strap, fixed to or proximate a distal end of said lateral cuff extension portion; and
   wherein said distal end of said lateral cuff extension portion, together with said second end of the tourniquet strap fixed thereto, are engageable with said tourniquet strap adjuster to secure, and coarsely tighten, said tourniquet cuff and tourniquet strap in a loop around said limb ready for tightening of said tourniquet strap by said tourniquet strap tensioner; and
   further comprising a tourniquet strap storage component configured to receive and store, in a folded configuration, said lateral cuff extension portion together with a portion of said tourniquet strap carried thereon.

11. The accessory of claim 10, wherein said strap adjuster comprises a buckle.

12. The accessory of claim 11, further comprising hook and loop fastener arranged on portions of an outer wall of said tourniquet cuff to allow said lateral cuff extension to be fed through said buckle to be secured back on said tourniquet cuff by fastening together said portions of the outer wall.

13. The accessory of claim 10, wherein said tourniquet strap storage component comprises a sleeve or pocket and further comprising hook and loop fastener disposed on the lateral cuff extension and on the inside of the pocket or sleeve for releaseably securing said lateral cuff extension portion stored inside said pocket or sleeve.

14. The accessory of claim 10,
   wherein said surfboard leash cuff band together with said lateral cuff extension portion define a hollow interior extending along said tourniquet cuff, and wherein a substantial portion of said tourniquet strap extending between the first and second fixed ends thereof is freely housed inside an interior of said tourniquet cuff such that the tourniquet strap is movable by the tourniquet strap tensioner to adjust the circumference of the strap loop.

15. The accessory of claim 14, wherein said tourniquet strap tensioner comprises a windlass bar threaded via an aperture thereof onto a twistable portion of said tourniquet strap; and
   wherein an outer wall of said surfboard leash cuff band has an opening into the interior of the tourniquet cuff to expose said twistable portion of said tourniquet strap and allow access to and operate said windlass bar threaded on said strap.

16. The accessory of claim 1, further comprises a surfboard leash cord attached to said surfboard leash cuff band via said surfboard leash cord attachment or interface.

17. The surfboard accessory of claim 1, wherein said tourniquet strap tensioner comprises any one of: a windlass bar, a ratchet mechanism/system, and an inflatable tube pneumatic system.

18. The surfboard accessory of claim 1, wherein said hybrid surfboard leash tourniquet further comprises a tourniquet strap adjuster.

19. The surfboard accessory of claim 18, wherein said tourniquet strap adjuster comprises a buckle.

20. A surfboard accessory comprising:
a hybrid surfboard leash tourniquet;
wherein said hybrid surfboard leash tourniquet comprises:
a surfboard leash cuff band;
a surfboard leash cuff band fastener carried on said surfboard leash cuff band for closing the cuff band in a loop around an ankle of a surfer;
a surfboard leash cord attachment or interface configured to releaseably or permanently attach a surfboard leash cord to said surfboard leash cuff band; and
a tourniquet strap adjuster; and
wherein said tourniquet strap adjuster is carried on said surfboard leash cuff band in addition to said surfboard leash cuff band fastener.

21. The surfboard accessory of claim 20, wherein said tourniquet strap adjuster comprises a buckle.

22. A kit of parts for assembling a surfboard accessory comprising a hybrid surfboard leash tourniquet, the kit of parts comprising;
a surfboard leash cuff band;
a surfboard leash cuff band fastener carried or carriable on said surfboard leash cuff band for closing the cuff band in a loop around an ankle of a surfer;
a surfboard leash cord attachment or interface configured to releaseably or permanently attach a surfboard leash cord to said surfboard leash cuff band; and
a tourniquet strap tensioner;
wherein said tourniquet strap tensioner is carried or carriable on said surfboard leash cuff band in addition to said surfboard leash cuff band fastener;
and
wherein, on assembly of the kit of parts, the surfboard accessory is operable as a surfboard leash cuff band, and the surfboard accessory is operable as a tourniquet for controlling extremity blood flow in the limb.

23. The kit of parts of claim 22, further comprising a box or bag, and an instruction manual for assembling said surfboard accessory from said kit of parts; wherein said kit of parts and said instruction manual are carried in said box or bag.

24. The surfboard accessory of claim 22, wherein said tourniquet strap tensioner comprises any one of: a windlass bar, a ratchet mechanism/system, and an inflatable tube pneumatic system.

25. A kit of parts for assembling a surfboard accessory comprising a hybrid surfboard leash tourniquet, the kit of parts comprising;
a surfboard leash cuff band;
a surfboard leash cuff band fastener carried or carriable on said surfboard leash cuff band for closing the cuff band in a loop around an ankle of a surfer;
a surfboard leash cord attachment or interface configured to releaseably or permanently attach a surfboard leash cord to said surfboard leash cuff band;
a tourniquet strap adjuster; and
wherein said tourniquet strap adjuster is carried or carriable on said surfboard leash cuff band in addition to said surfboard leash cuff band fastener;
and
wherein, on assembly of the kit of parts, the surfboard accessory is operable as a surfboard leash cuff band, and the surfboard accessory is operable as a tourniquet for controlling extremity blood flow in the limb.

26. The kit of parts of claim 25, further comprising a box or bag, and an instruction manual for assembling said surfboard accessory from said kit of parts; wherein said kit of parts and said instruction manual are carried in said box or bag.

27. The surfboard accessory of claim 25, wherein said tourniquet strap adjuster comprises a buckle.

* * * * *